(12) United States Patent
Shelton, IV et al.

(10) Patent No.: US 7,721,931 B2
(45) Date of Patent: May 25, 2010

(54) PREVENTION OF CARTRIDGE REUSE IN A SURGICAL INSTRUMENT

(75) Inventors: Frederick E. Shelton, IV, New Vienna, OH (US); James R. Giordano, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 573 days.

(21) Appl. No.: 11/651,768

(22) Filed: Jan. 10, 2007

(65) Prior Publication Data

US 2008/0164296 A1 Jul. 10, 2008

(51) Int. Cl.
*A61B 17/068* (2006.01)

(52) U.S. Cl. .................. 227/176.1; 227/19; 227/180.1; 606/219

(58) Field of Classification Search .................. 227/19, 227/176.1, 175.1, 179.1, 180.1; 606/219, 606/139
See application file for complete search history.

(56) References Cited

U.S. PATENT DOCUMENTS

| 3,490,675 | A | 1/1970 | Green et al. |
|---|---|---|---|
| 3,643,851 | A | 2/1972 | Green et al. |
| 3,662,939 | A | 5/1972 | Bryan |
| 3,717,294 | A | 2/1973 | Green |
| 3,819,100 | A | 6/1974 | Noiles et al. |
| 4,331,277 | A | 5/1982 | Green |
| 4,383,634 | A | 5/1983 | Green |
| 4,396,139 | A | 8/1983 | Hall et al. |
| 4,402,445 | A | 9/1983 | Green |
| 4,415,112 | A | 11/1983 | Green |
| 4,429,695 | A | 2/1984 | Green |
| 4,475,679 | A | 10/1984 | Fleury, Jr. |
| 4,500,024 | A | 2/1985 | DiGiovanni et al. |
| 4,505,273 | A | 3/1985 | Braun et al. |
| 4,505,414 | A | 3/1985 | Filipi |
| 4,522,327 | A | 6/1985 | Korthoff et al. |
| 4,530,453 | A | 7/1985 | Green |
| 4,566,620 | A | 1/1986 | Green et al. |
| 4,573,622 | A | 3/1986 | Green et al. |
| 4,580,712 | A | 4/1986 | Green |
| 4,610,383 | A | 9/1986 | Rothfuss et al. |
| 4,629,107 | A | 12/1986 | Fedotov et al. |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Scott A. Smith
(74) *Attorney, Agent, or Firm*—Dean Garner

(57) ABSTRACT

A surgical instrument is disclosed. The surgical instrument includes a control unit and a staple cartridge including a transponder. The control unit is configured to transmit a first wireless signal to the transponder and to receive a second wireless signal from the transponder to determine one of a first electronic state and a second electronic state of the transponder based on the second wireless signal.

18 Claims, 20 Drawing Sheets

U.S. PATENT DOCUMENTS

| | | |
|---|---|---|
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,383,880 A | 1/1995 | Hooven |
| 5,395,033 A | 3/1995 | Byrne et al. |
| 5,397,324 A | 3/1995 | Carroll et al. |
| 5,425,745 A | 6/1995 | Green et al. |
| 5,433,721 A | 7/1995 | Hooven et al. |
| 5,465,895 A | 11/1995 | Knodel et al. |
| 5,474,566 A | 12/1995 | Alesi et al. |
| 5,478,354 A | 12/1995 | Tovey et al. |
| 5,480,089 A | 1/1996 | Blewett |
| 5,484,451 A | 1/1996 | Akopov et al. |
| 5,485,947 A | 1/1996 | Olson et al. |
| 5,487,499 A | 1/1996 | Sorrentino et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,518,163 A | 5/1996 | Hooven |
| 5,518,164 A | 5/1996 | Hooven |
| 5,529,235 A | 6/1996 | Boiarski et al. |
| 5,535,934 A | 7/1996 | Boiarski et al. |
| 5,543,119 A | 8/1996 | Sutter et al. |
| 5,553,765 A | 9/1996 | Knodel et al. |
| 5,554,169 A | 9/1996 | Green et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,702,408 A | 12/1997 | Wales et al. |
| 5,704,534 A | 1/1998 | Huitema et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,256 A | 6/1998 | Mastri et al. |
| 5,779,130 A | 7/1998 | Alesi et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,807,393 A | 9/1998 | Williamson, IV et al. |
| 5,817,093 A | 10/1998 | Williamson, IV et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,868,760 A | 2/1999 | McGuckin, Jr. |
| 5,897,562 A | 4/1999 | Bolanos et al. |
| 5,901,895 A | 5/1999 | Heaton et al. |
| 5,908,427 A | 6/1999 | McKean et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,941,442 A | 8/1999 | Geiste et al. |

| Patent No. | Date | Inventor(s) |
|---|---|---|
| 5,954,259 A | 9/1999 | Viola et al. |
| 6,010,054 A | 1/2000 | Johnson et al. |
| 6,024,741 A | 2/2000 | Williamson, IV et al. |
| 6,032,849 A | 3/2000 | Mastri et al. |
| 6,045,560 A | 4/2000 | McKean et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,119,913 A | 9/2000 | Adams et al. |
| 6,126,058 A | 10/2000 | Adams et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,387,113 B1 | 5/2002 | Hawkins et al. |
| RE37,814 E | 8/2002 | Allgeyer |
| 6,436,107 B1 * | 8/2002 | Wang et al. .................. 606/139 |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,988 B2 | 10/2003 | Weadock |
| 6,644,532 B2 | 11/2003 | Green et al. |
| 6,666,875 B1 | 12/2003 | Sakurai et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,793,652 B1 | 9/2004 | Whitman et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Ratcliff et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,108,695 B2 | 9/2006 | Witt et al. |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,128,253 B2 | 10/2006 | Mastri et al. |
| 7,140,527 B2 | 11/2006 | Ehrenfels et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,546,940 B2 | 6/2009 | Milliman et al. |
| 2002/0117534 A1 | 8/2002 | Green et al. |
| 2003/0093103 A1 | 5/2003 | Malackowski et al. |
| 2003/0105478 A1 | 6/2003 | Whitman et al. |
| 2003/0130677 A1 | 7/2003 | Whitman et al. |

| | | | | | |
|---|---|---|---|---|---|
| 2004/0006372 A1 | 1/2004 | Racenet et al. | 2008/0029573 A1 | 2/2008 | Shelton et al. |
| 2004/0034369 A1 | 2/2004 | Sauer et al. | 2008/0029574 A1 | 2/2008 | Shelton et al. |
| 2004/0094597 A1 | 5/2004 | Whitman et al. | 2008/0029575 A1 | 2/2008 | Shelton et al. |
| 2004/0108357 A1 | 6/2004 | Milliman et al. | 2008/0029576 A1 | 2/2008 | Shelton et al. |
| 2004/0116952 A1 | 6/2004 | Sakurai et al. | 2008/0035701 A1 | 2/2008 | Racenet et al. |
| 2004/0164123 A1 | 8/2004 | Racenet et al. | 2008/0041917 A1 | 2/2008 | Racenet et al. |
| 2004/0167572 A1 | 8/2004 | Roth et al. | 2008/0078800 A1 | 4/2008 | Hess et al. |
| 2004/0173659 A1 | 9/2004 | Green et al. | 2008/0078801 A1 | 4/2008 | Shelton et al. |
| 2004/0222268 A1 | 11/2004 | Bilotti et al. | 2008/0078802 A1 | 4/2008 | Hess et al. |
| 2004/0232201 A1 | 11/2004 | Wenchell et al. | 2008/0078803 A1 | 4/2008 | Shelton et al. |
| 2004/0243151 A1 | 12/2004 | Demmy et al. | 2008/0078804 A1 | 4/2008 | Shelton et al. |
| 2004/0254608 A1 | 12/2004 | Huitema et al. | 2008/0078806 A1 | 4/2008 | Omaits et al. |
| 2005/0059997 A1 | 3/2005 | Bauman et al. | 2008/0078807 A1 | 4/2008 | Hess et al. |
| 2005/0103819 A1 | 5/2005 | Racenet et al. | 2008/0078808 A1 | 4/2008 | Hess et al. |
| 2005/0119669 A1 | 6/2005 | Demmy | 2008/0082115 A1 | 4/2008 | Morgan et al. |
| 2005/0125009 A1 | 6/2005 | Perry et al. | 2008/0082124 A1 | 4/2008 | Hess et al. |
| 2005/0131390 A1 | 6/2005 | Heinrich et al. | 2008/0082125 A1 | 4/2008 | Murray et al. |
| 2005/0143759 A1 | 6/2005 | Kelly | 2008/0082126 A1 | 4/2008 | Murray et al. |
| 2005/0184121 A1 | 8/2005 | Heinrich | 2008/0167522 A1 | 7/2008 | Giordano et al. |
| 2005/0187576 A1 | 8/2005 | Whitman et al. | 2008/0167644 A1 | 7/2008 | Shelton et al. |
| 2005/0189397 A1 | 9/2005 | Jankowski | 2008/0167670 A1 | 7/2008 | Shelton et al. |
| 2005/0216055 A1 | 9/2005 | Scirica et al. | 2008/0167671 A1 | 7/2008 | Giordano et al. |
| 2005/0263563 A1 | 12/2005 | Racenet et al. | 2008/0167672 A1 | 7/2008 | Giordano et al. |
| 2005/0274768 A1 | 12/2005 | Cummins et al. | 2008/0167736 A1 | 7/2008 | Swayze et al. |
| 2006/0011699 A1 | 1/2006 | Olson et al. | 2008/0169328 A1 | 7/2008 | Shelton |
| 2006/0025812 A1 | 2/2006 | Shelton, IV | 2008/0169329 A1 | 7/2008 | Shelton et al. |
| 2006/0047307 A1 | 3/2006 | Ortiz et al. | 2008/0169330 A1 | 7/2008 | Shelton et al. |
| 2006/0049229 A1 | 3/2006 | Milliman et al. | 2008/0169331 A1 | 7/2008 | Shelton et al. |
| 2006/0052825 A1 | 3/2006 | Ransick et al. | 2008/0169332 A1 | 7/2008 | Shelton et al. |
| 2006/0085033 A1 | 4/2006 | Criscuolo et al. | 2008/0169333 A1 | 7/2008 | Shelton et al. |
| 2006/0100643 A1 | 5/2006 | Laufer et al. | 2008/0210738 A1 | 9/2008 | Shelton et al. |
| 2006/0108393 A1 | 5/2006 | Heinrich et al. | 2008/0237296 A1 | 10/2008 | Boudreaux et al. |
| 2006/0151567 A1 | 7/2006 | Roy | 2008/0296343 A1 | 12/2008 | Schall et al. |
| 2006/0180634 A1 | 8/2006 | Shelton et al. | 2008/0296345 A1 | 12/2008 | Shelton, IV et al. |
| 2006/0226196 A1 | 10/2006 | Hueil et al. | 2008/0296346 A1 | 12/2008 | Shelton, IV et al. |
| 2006/0241692 A1 | 10/2006 | McGuckin, Jr. et al. | 2008/0296347 A1 | 12/2008 | Shelton, IV et al. |
| 2006/0273135 A1 | 12/2006 | Beetel | 2008/0300579 A1 | 12/2008 | Broehl et al. |
| 2006/0278680 A1 | 12/2006 | Viola et al. | 2008/0300580 A1 | 12/2008 | Shelton, IV et al. |
| 2006/0278681 A1 | 12/2006 | Viola et al. | 2008/0300613 A1 | 12/2008 | Shelton, IV et al. |
| 2006/0289602 A1 | 12/2006 | Wales et al. | 2008/0308601 A1 | 12/2008 | Timm et al. |
| 2007/0023477 A1 | 2/2007 | Whitman et al. | 2008/0308602 A1 | 12/2008 | Timm et al. |
| 2007/0034668 A1 | 2/2007 | Holsten et al. | 2008/0308603 A1 | 12/2008 | Shelton, IV et al. |
| 2007/0045379 A1 | 3/2007 | Shelton, IV | 2008/0308606 A1 | 12/2008 | Timm et al. |
| 2007/0084897 A1 | 4/2007 | Shelton, IV et al. | 2008/0308607 A1 | 12/2008 | Timm et al. |
| 2007/0102452 A1 | 5/2007 | Shelton, IV et al. | 2008/0308608 A1 | 12/2008 | Prommersberger |
| 2007/0102453 A1 | 5/2007 | Morgan et al. | 2008/0314954 A1 | 12/2008 | Boudreaux |
| 2007/0102472 A1 | 5/2007 | Shelton, IV | 2008/0314955 A1 | 12/2008 | Boudreaux et al. |
| 2007/0102473 A1 | 5/2007 | Shelton, IV et al. | 2008/0314956 A1 | 12/2008 | Boudreaux |
| 2007/0102474 A1 | 5/2007 | Shelton, IV et al. | 2008/0314957 A1 | 12/2008 | Boudreaux |
| 2007/0106317 A1 | 5/2007 | Shelton, IV et al. | 2008/0314961 A1 | 12/2008 | Boudreaux et al. |
| 2007/0114261 A1 | 5/2007 | Ortiz et al. | 2008/0314962 A1 | 12/2008 | Boudreaux |
| 2007/0158385 A1 | 7/2007 | Hueil et al. | 2009/0001121 A1 | 1/2009 | Hess et al. |
| 2007/0170225 A1 | 7/2007 | Shelton, IV et al. | 2009/0001123 A1 | 1/2009 | Morgan et al. |
| 2007/0175949 A1 | 8/2007 | Shelton, IV et al. | 2009/0001124 A1 | 1/2009 | Hess et al. |
| 2007/0175950 A1 | 8/2007 | Shelton, IV et al. | 2009/0001125 A1 | 1/2009 | Hess et al. |
| 2007/0175951 A1 | 8/2007 | Shelton, IV et al. | 2009/0001126 A1 | 1/2009 | Hess et al. |
| 2007/0175953 A1 | 8/2007 | Shelton, IV et al. | 2009/0001128 A1 | 1/2009 | Weisenburgh, II et al. |
| 2007/0175955 A1 | 8/2007 | Shelton, IV et al. | 2009/0001130 A1 | 1/2009 | Hess et al. |
| 2007/0175956 A1 | 8/2007 | Swayze et al. | 2009/0005807 A1 | 1/2009 | Hess et al. |
| 2007/0175957 A1 | 8/2007 | Shelton, IV et al. | 2009/0005808 A1 | 1/2009 | Hess et al. |
| 2007/0175958 A1 | 8/2007 | Shelton, IV et al. | 2009/0005809 A1 | 1/2009 | Hess et al. |
| 2007/0175959 A1 | 8/2007 | Shelton, IV et al. | 2009/0012556 A1 | 1/2009 | Boudreaux et al. |
| 2007/0175964 A1 | 8/2007 | Shelton, IV et al. | 2009/0076534 A1 | 3/2009 | Shelton, IV et al. |
| 2007/0179476 A1 | 8/2007 | Shelton, IV et al. | 2009/0200355 A1 | 8/2009 | Baxter, III et al. |
| 2007/0181632 A1 | 8/2007 | Milliman | 2009/0206123 A1 | 8/2009 | Doll et al. |
| 2007/0194079 A1 | 8/2007 | Hueil et al. | 2009/0206124 A1 | 8/2009 | Hall et al. |
| 2007/0194080 A1 | 8/2007 | Swayze et al. | 2009/0206125 A1 | 8/2009 | Huitema et al. |
| 2007/0194081 A1 | 8/2007 | Hueil et al. | 2009/0206126 A1 | 8/2009 | Huitema et al. |
| 2007/0194082 A1 | 8/2007 | Morgan et al. | 2009/0206128 A1 | 8/2009 | Hueil et al. |
| 2007/0233053 A1 | 10/2007 | Shelton, IV et al. | 2009/0206129 A1 | 8/2009 | Doll et al. |
| 2007/0246505 A1 | 10/2007 | Pace-Floridia et al. | 2009/0206130 A1 | 8/2009 | Hall et al. |
| 2007/0295780 A1 | 12/2007 | Shelton et al. | 2009/0206131 A1 | 8/2009 | Weisenburgh, II et al. |
| 2008/0029570 A1 | 2/2008 | Shelton et al. | 2009/0206132 A1 | 8/2009 | Hueil et al. |

| | | | |
|---|---|---|---|
| 2009/0206133 A1 | 8/2009 | Morgan et al. | |
| 2009/0206134 A1 | 8/2009 | Swayze et al. | |
| 2009/0206135 A1 | 8/2009 | Hall et al. | |
| 2009/0206136 A1 | 8/2009 | Moore et al. | |
| 2009/0206137 A1 | 8/2009 | Hall et al. | |
| 2009/0206138 A1 | 8/2009 | Smith et al. | |
| 2009/0206139 A1 | 8/2009 | Hall et al. | |
| 2009/0206140 A1 | 8/2009 | Scheib et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0206144 A1 | 8/2009 | Doll et al. | |
| 2009/0209946 A1 | 8/2009 | Swayze et al. | |
| 2009/0255974 A1 | 10/2009 | Viola | |
| 2009/0255978 A1 | 10/2009 | Viola et al. | |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1300117 B1 | 8/2007 |
| EP | 1813199 A1 | 8/2007 |
| EP | 1813207 A1 | 8/2007 |
| EP | 1872727 A1 | 1/2008 |
| EP | 1839596 A2 | 2/2008 |
| EP | 1897502 A1 | 3/2008 |
| EP | 1759645 B1 | 11/2008 |
| EP | 1749486 B1 | 3/2009 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/35464 A1 | 11/1996 |
| WO | WO 97/34533 A1 | 9/1997 |
| WO | WO 97/39688 A2 | 10/1997 |
| WO | WO 98/30153 A1 | 7/1998 |

| | | | |
|---|---|---|---|
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/010482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/016290 A2 | 2/2007 |
| WO | WO 2007/018898 A2 | 2/2007 |
| WO | WO 2007/121579 A1 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

* cited by examiner

PREVENTION OF CARTRIDGE REUSE IN A SURGICAL INSTRUMENT

CROSS-REFERENCE TO RELATED APPLICATIONS

The present application is related to the following, concurrently-filed U.S. patent applications, which are incorporated herein by reference in their entirety:

(1) U.S. patent application Ser. No. 11/651,715, entitled "SURGICAL INSTRUMENT WITH WIRELESS COMMUNICATION BETWEEN CONTROL UNIT AND SENSOR TRANSPONDERS," by J. Giordano et al.;

(2) U.S. patent application Ser. No. 11/651,807, entitled "SURGICAL INSTRUMENT WITH WIRELESS COMMUNICATION BETWEEN CONTROL UNIT AND REMOTE SENSOR," by J. Giordano et al.;

(3) U.S. patent application Ser. No. 11/651,806, entitled "SURGICAL INSTRUMENT WITH ELEMENTS TO COMMUNICATE BETWEEN CONTROL UNIT AND END EFFECTOR," by J. Giordano et al.;

(4) U.S. patent application Ser. No. 11/651,771, entitled "POST-STERILIZATION PROGRAMMING OF SURGICAL INSTRUMENTS," by J. Swayze et al.;

(5) U.S. patent application Ser. No. 11/651,788, entitled "INTERLOCK AND SURGICAL INSTRUMENT INCLUDING SAME, by F. Shelton et al.; and (6) U.S. patent application Ser. No. 11/651,785, entitled "SURGICAL INSTRUMENT WITH ENHANCED BATTERY PERFORMANCE," by F. Shelton et al..

FIELD OF THE INVENTION

The disclosed invention relates generally and in various embodiments to surgical stapling and cutting instruments structured and configured for applying lines of staples from a staple cartridge into tissue while cutting the tissue between the applied staple lines. More particularly the disclosed invention relates to electronic controls for use in motorized surgical stapling and cutting instruments that prevent cutting of the tissue when a spent staple cartridge (or no staple cartridge) is present in the instrument and limit use of the instruments to a predetermined number of stapling and cutting operations.

BACKGROUND

Endoscopic surgical instruments are often preferred over traditional open surgical devices since a smaller incision tends to reduce post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Advantageously, the design of the end effector may be such that it can be reused with the surgical stapler. For instance, one patient may need a series of severing and stapling operations. Replacing an entire end effector for each operation tends to be economically inefficient, especially if the end effector is built for strength and reliability over repeated operations. To that end, the staple cartridge is typically configured to be disposable and is fitted into the end effector prior to each operation of the surgical stapler.

An example of a surgical stapler suitable for endoscopic applications is described in U.S. Pat. No. 5,465,895, entitled "SURGICAL STAPLER INSTRUMENT" to Knodel et al., which discloses an endocutter with distinct closing and firing actions. Thereby, a clinician is able to close the jaw members upon tissue to position the tissue prior to firing. Once the clinician has determined that the jaw members are properly gripping tissue, the clinician can then fire the surgical stapler with either a single firing stroke or multiple firing strokes, depending on the device. Firing the surgical stapler causes severing and stapling of the tissue. The simultaneous severing and stapling avoids complications that may arise when performing such actions sequentially with different surgical tools that respectively only sever and staple.

One specific advantage of being able to close upon tissue before firing is that the clinician is able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Because the actuating force (i.e., the "force-to-fire", or FTF) necessary to close the jaws and simultaneously perform the cutting and stapling operation may be considerable, a manually-powered cutting and stapling instrument such as that described above may not be utilizable by otherwise qualified operators who are unable to generate the required FTF. Accordingly, powered cutting and stapling instruments have been developed for decreasing the force-to-fire (FTF). Such instruments typically incorporate motors or other actuating mechanisms suitable for supplementing or replacing operator-generated force for performing the cutting and stapling operation.

Although powered instruments provide numerous advantages, it is desirable to prevent inadvertent firing of the instrument under certain conditions. For example, firing the instrument without having a staple cartridge installed, or firing the instrument having an installed but spent (e.g., previously fired) staple cartridge, may result in cutting of tissue without simultaneous stapling to minimize bleeding. Electronic controls, or interlocks, for preventing powered endocutter operation under such conditions have heretofore utilized active electrical circuits disposed in the end effector for determining whether an unspent staple cartridge has been installed in the end effector. For example, U.S. Pat. No. 5,529,235 entitled IDENTIFICATION DEVICE FOR SURGICAL STAPLING INSTRUMENT to Boiarski et al. discloses an interlock circuit integral to the staple cartridge and having a fuse that is opened responsive to a mechanical force or electrical current applied thereto concurrent with a firing operation. The open electrical state of the fuse is detected via a hardwired control circuit externally located with respect to the end effector to prevent a subsequent firing operation using a spent staple cartridge. In this way, opening the fuse disables the staple cartridge and prevents its reuse.

U.S. patent application Ser. No. 11/343,439 entitled "ELECTRONIC INTERLOCKS AND SURGICAL INSTRUMENT INCLUDING SAME" to Swayze et al. discloses the use of electronic sensors disposed within the end effector for determining if an unspent staple cartridge has been installed. The sensors may include switches connected in series with a motor or other electrically-powered actuation mechanism such that current flow necessary for generating the actuation force is prevented when the staple cartridge is not installed, or when the staple cartridge is installed but spent.

Although the above-described electronic controls are generally effective for preventing inadvertent instrument operation, placement of electronics in the end effector has heretofore required electrical cabling to connect the end effector with other electrical components (e.g., power sources, motors, control circuits, etc.) externally located with respect to the end effector. In cases where such electrical components are disposed within a handle of the instrument (as in the above-described references), the electrical cabling is typically routed via a shaft connecting the end effector to the handle. However, routing electrical cabling in this manner is inconvenient and increases instrument complexity and cost.

In addition to preventing firing of the instrument in the absence of an unspent staple cartridge, it may further be desirable to limit the number of firing operations that may be performed by the instrument.

Consequently, a significant need exists for electronic controls for use in powered cutting and stapling instruments that prevent inadvertent firing (e.g., cutting but not stapling) while avoiding complexities associated with hardwired end effector electronics, and that limit instrument use to a predetermined number of firing operations.

SUMMARY

This application discloses a surgical instrument. In one embodiment, the surgical instrument includes a control unit and a staple cartridge including a transponder. The control unit is configured to transmit a first wireless signal to the transponder and to receive a second wireless signal from the transponder to determine one of a first electronic state and a second electronic state of the transponder based on the second wireless signal.

In another embodiment, the instrument includes an end effector comprising a moveable cutting instrument to cut an object, and a motor coupled to the end effector to actuate the cutting instrument. Each actuation of the cutting instrument corresponding to a firing operation by the surgical instrument. The surgical instrument further includes a control unit to count a number of firing operations by the surgical instrument and to electronically alter at least one component of the instrument when the number of firing operations is equal to a predetermined number. The altered at least one component prevents firing operations by the surgical instrument in excess of the predetermined number.

This application further discloses a staple cartridge for use in a surgical instrument. The staple cartridge includes a transponder transitionable from a first electronic state to a second electronic state. The first electronic state is indicative of an unfired state of the staple cartridge and the second electronic state is indicative of a fired state of the staple cartridge.

DRAWINGS

Various embodiments of the present invention are described herein by way of example in conjunction with the following figures, wherein.

DETAILED DESCRIPTION

Various embodiments of the present invention are directed generally to a surgical instrument having at least one transponder and means for communicating power and/or data signals to the transponder(s) from a control unit. The present invention may be used with any type of surgical instrument comprising at least one transponder, such as endoscopic or laparoscopic surgical instruments, but is particularly useful for surgical instruments where some feature of the instrument, such as a free rotating joint, prevents or otherwise inhibits the use of a wired connection to the sensor(s). Before describing aspects of the system, one type of surgical instrument in which embodiments of the present invention may be used—an endoscopic stapling and cutting instrument (i.e., an endocutter)—is first described by way of illustration.

Figure 1:
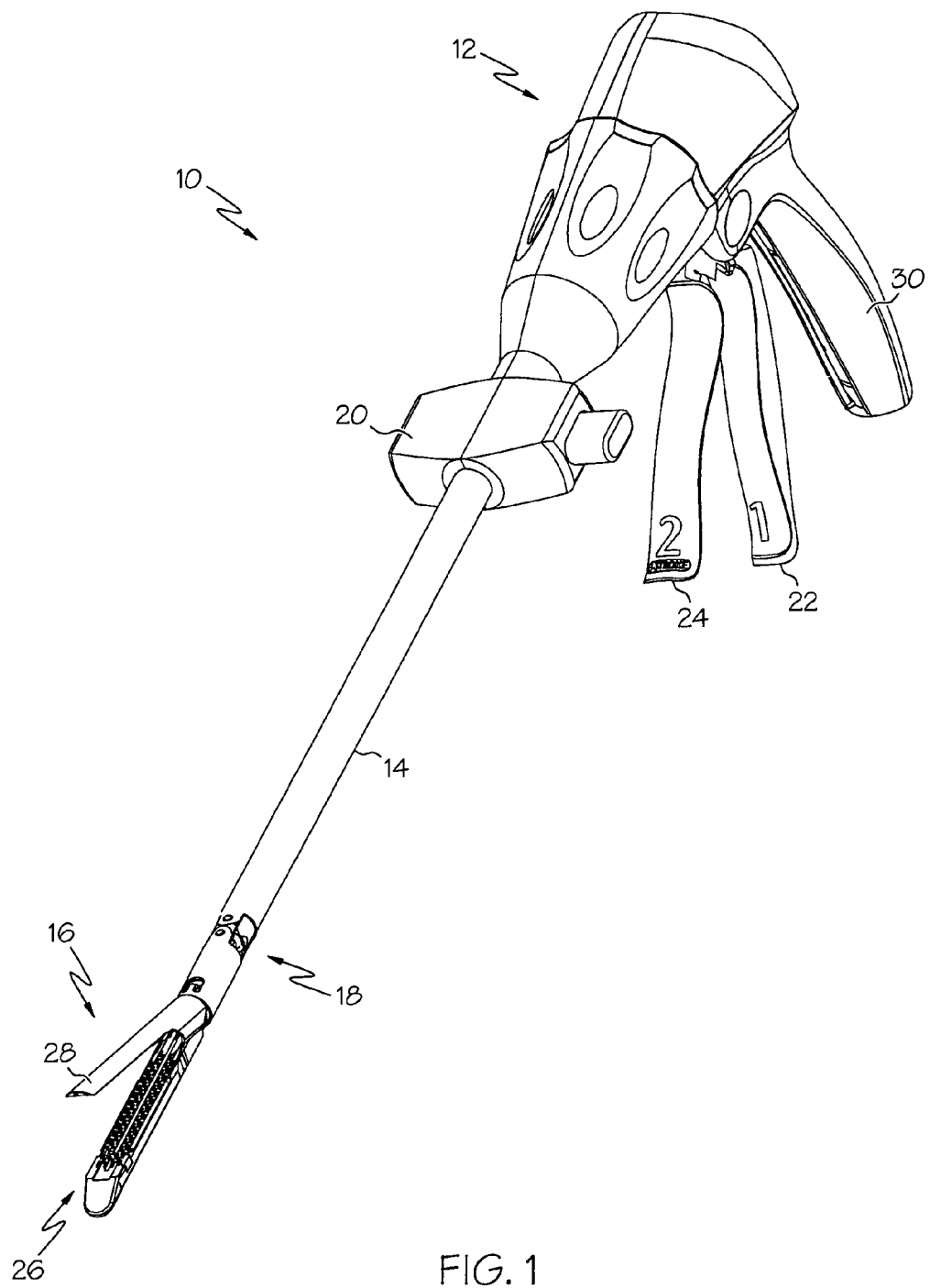
FIGS. 1 and 2 are perspective views of a surgical instrument according to various embodiments of the present invention.
Figure 2:
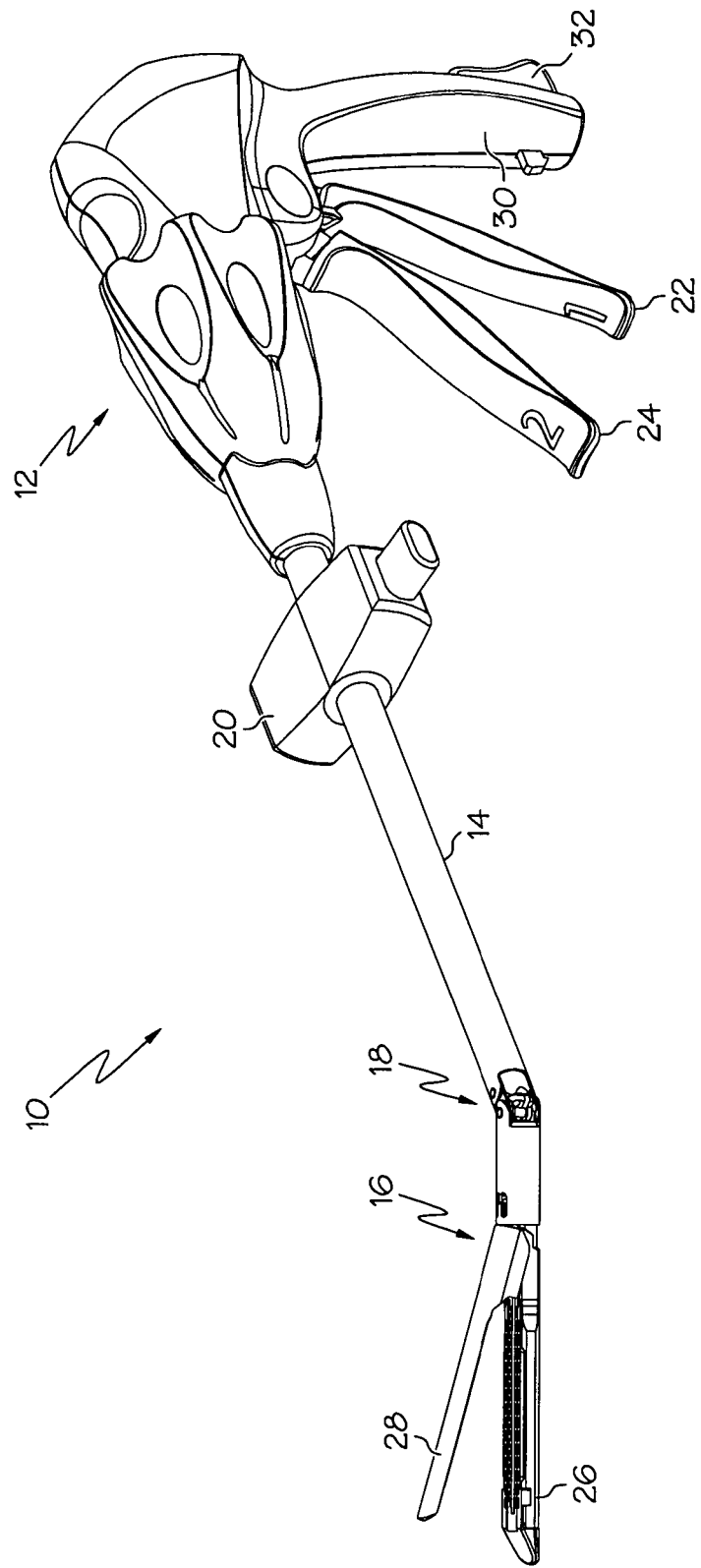

FIGS. 1 and 2 depict a surgical cutting and fastening instrument 10 according to various embodiments of the present invention. The illustrated embodiment is an endoscopic instrument and, in general, the embodiments of the instrument 10 described herein are endoscopic surgical cutting and fastening instruments. It should be noted, however, that according to other embodiments of the present invention, the instrument may be a non-endoscopic surgical cutting and fastening instrument, such as a laparoscopic instrument.

The surgical instrument 10 depicted in FIGS. 1 and 2 comprises a handle 12, a shaft 14, and an articulating end effector 16 pivotally connected to the shaft 14 at an articulation pivot 18. Correct placement and orientation of the end effector 16 may be facilitated by controls on the handle 12, including (1) a rotation knob 17 for rotating the closure tube (described in more detail below in connection with FIGS. 4-5) at a free rotating joint 19 of the shaft 14 to thereby rotate the end effector 16 and (2) an articulation control 20 to effect rotational articulation of the end effector 16 about the articulation pivot 18. In the illustrated embodiment, the end effector 16 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc.

The handle 12 of the instrument 10 may include a closure trigger 22 and a firing trigger 24 for actuating the end effector 16. It will be appreciated that instruments having end effectors directed to different surgical tasks may have different numbers or types of triggers or other suitable controls for operating the end effector 16. The end effector 16 is shown separated from the handle 12 by a preferably elongate shaft 14. In one embodiment, a clinician or operator of the instrument 10 may articulate the end effector 16 relative to the shaft 14 by utilizing the articulation control 20 as described in more detail in pending U.S. patent application Ser. No. 11/329,020 entitled "SURGICAL INSTRUMENT HAVING AN ARTICULATING END EFFECTOR" to Hueil et al., which is incorporated herein by reference.

The end effector 16 includes in this example, among other things, a staple channel 26 and a pivotally translatable clamping member, such as an anvil 28, which are maintained at a spacing that assures effective stapling and severing of tissue clamped in the end effector 16. The handle 12 includes a pistol grip 30 towards which a closure trigger 22 is pivotally drawn by the clinician to cause clamping or closing of the anvil 28 toward the staple channel 26 of the end effector 16 to thereby clamp tissue positioned between the anvil 28 and the channel 26. The firing trigger 24 is farther outboard of the closure trigger 22. Once the closure trigger 22 is locked in the closure position as further described below, the firing trigger 24 may rotate slightly toward the pistol grip 30 so that it can be reached by the operator using one hand. The operator may then pivotally draw the firing trigger 24 toward the pistol grip 30 to cause the stapling and severing of clamped tissue in the end effector 16. In other embodiments, different types of clamping members besides the anvil 28 may be used, such as, for example, an opposing jaw, etc.

It will be appreciated that the terms "proximal" and "distal" are used herein with reference to a clinician gripping the handle 12 of an instrument 10. Thus, the end effector 16 is distal with respect to the more proximal handle 12. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 22 may be actuated first. Once the clinician is satisfied with the positioning of the end effector 16, the clinician may draw back the closure trigger 22 to its fully closed, locked position proximate to the pistol grip 30. The firing trigger 24 may then be actuated. The firing trigger 24 returns to the open position (shown in FIGS. 1 and 2) when the clinician removes pressure, as described more fully below. A release button 32 on the handle 12, when depressed, may release the locked closure trigger 22. Various configurations for locking and unlocking the closure trigger 22 using the release button 32 are described in pending U.S. patent application Ser. No. 11/343,573 entitled "MOTOR-DRIVEN SURGICAL CUTTING AND FASTENING INSTRUMENT WITH LOADING FORCE FEEDBACK" to Shelton, IV et al., which is incorporated herein by reference.

Figure 3:
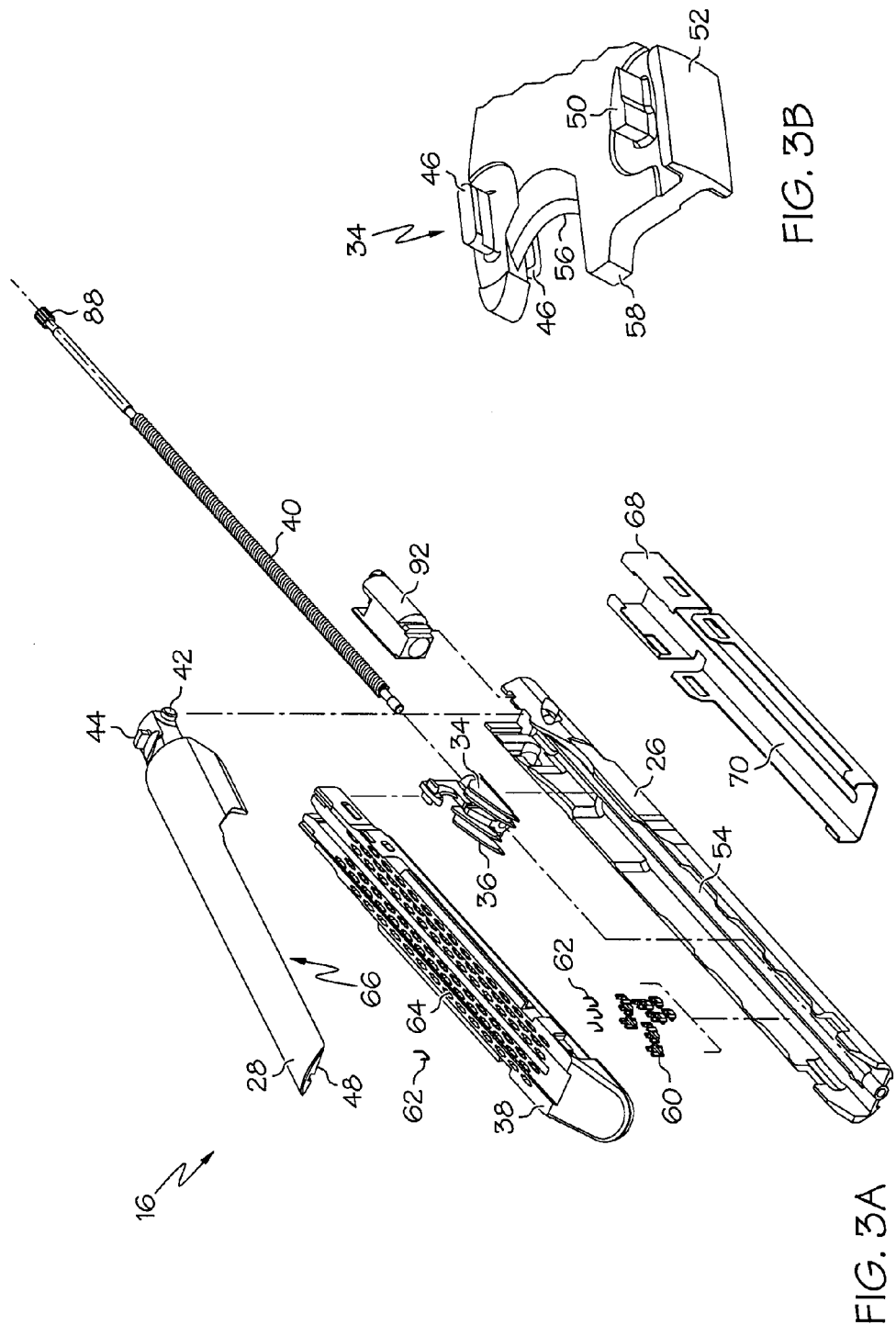
FIG. 3A is an exploded view of the end effector according to various embodiments of the present invention.
FIG. 3B is a perspective view of the cutting instrument of FIG. 3A.

FIG. 3A is an exploded view of the end effector 16 according to various embodiments, and FIG. 3B is a perspective view of the cutting instrument of FIG. 3A. As shown in the illustrated embodiment, the end effector 16 may include, in addition to the previously-mentioned channel 26 and anvil 28, a cutting instrument 34, a staple cartridge 38 that is removably seated (e.g., installed) in the channel 26, a sled 36 disposed within the staple cartridge 38, and a helical screw shaft 40.

The anvil 28 may be pivotably opened and closed at a pivot point 42 connected to the proximate end of the channel 26. The anvil 28 may also include a tab 44 at its proximate end that is inserted into a component of the mechanical closure system (described further below) to open and close the anvil 28. When the closure trigger 22 is actuated, that is, drawn in by an operator of the instrument 10, the anvil 28 may pivot about the pivot point 42 into the clamped or closed position. If clamping of the end effector 16 is satisfactory, the operator may actuate the firing trigger 24, which, as explained in more detail below, causes the cutting instrument 34 to travel longitudinally along the channel 26.

As shown, the cutting instrument 34 includes upper guide pins 46 that enter an anvil slot 48 in the anvil 28 to verify and assist in maintaining the anvil 28 in a closed state during staple formation and severing. Spacing between the channel 26 and anvil 28 is further maintained by the cutting instrument 34 by having middle pins 50 slide along the top surface of the channel 26 while a bottom foot 52 opposingly slides along the undersurface of the channel 26, guided by a longitudinal opening 54 in the channel 26. A distally presented cutting surface 56 between the upper guide pins 46 and middle pins 50 severs clamped tissue while distally-presented surface 58 actuates the staple cartridge 38 by engaging and progressively driving the sled 36 through the staple cartridge 38 from an unfired position located at a proximal end of the staple cartridge 38 to a fired position located at a distal end of the staple cartridge 38. When the sled 36 is in the unfired position, the staple cartridge 38 is in an unfired, or unspent, state. When the sled 36 is in the fired position, the staple cartridge 38 is in a fired, or spent, state. Actuation of the staple cartridge 38 causes staple drivers 60 to cam upwardly, driving staples 62 out of upwardly open staple holes 64 formed in the staple cartridge 38. The staples 62 are subsequently formed against a staple forming undersurface 66 of the anvil 28. A staple cartridge tray 68 encompasses from the bottom the other components of the staple cartridge 38 to hold them in place. The staple cartridge tray 68 includes a rearwardly open slot 70 that overlies the longitudinal opening 54 in the channel 26. A lower surface of the staple cartridge 38 and an upward surface of the channel 26 form a firing drive slot 200 (FIG. 6) through which the middle pins 50 pass during distal and proximal movement of the cutting instrument 34. The sled 36 may be an integral component of the staple cartridge 38 such that when the cutting instrument 34 retracts following the cutting operation, the sled 36 does not retract. U.S. Pat. No. 6,978,921, entitled "SURGICAL STAPLING INSTRU- MENT INCORPORATING AN E-BEAM FIRING MECHANISM" to Shelton, IV et al., which is incorporated herein by reference, provides more details about such two-stroke cutting and fastening instruments.

It should be noted that although the embodiments of the instrument 10 described herein employ an end effector 16 that staples the severed tissue, in other embodiments different techniques for fastening or sealing the severed tissue may be used. For example, end effectors that use RF energy or adhesives to fasten the severed tissue may also be used. U.S. Pat. No. 5,709,680 entitled "ELECTROSURGICAL HEMOSTATIC DEVICE" to Yates et al., and U.S. Pat. No. 5,688,270 entitled "ELECTOSURGICAL HEMOSTATIC DEVICE WITH RECESSED AND/OR OFFSET ELECTRODES" to Yates et al., both of which are incorporated herein by reference, disclose cutting instruments that uses RF energy to fasten the severed tissue. U.S. patent application Ser. No. 11/267,811 entitled "SURGICAL STAPLING INSTRUMENTS STRUCTURED FOR DELIVERY OF MEDICAL AGENTS" to Morgan et al., and U.S. patent application Ser. No. 11/267,383 entitled "SURGICAL STAPLING INSTRUMENTS STRUCTURED FOR PUMP-ASSISTED DELIVERY OF MEDICAL AGENTS" to Shelton IV et al., both of which are also incorporated herein by reference, disclose cutting instruments that uses adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 4:
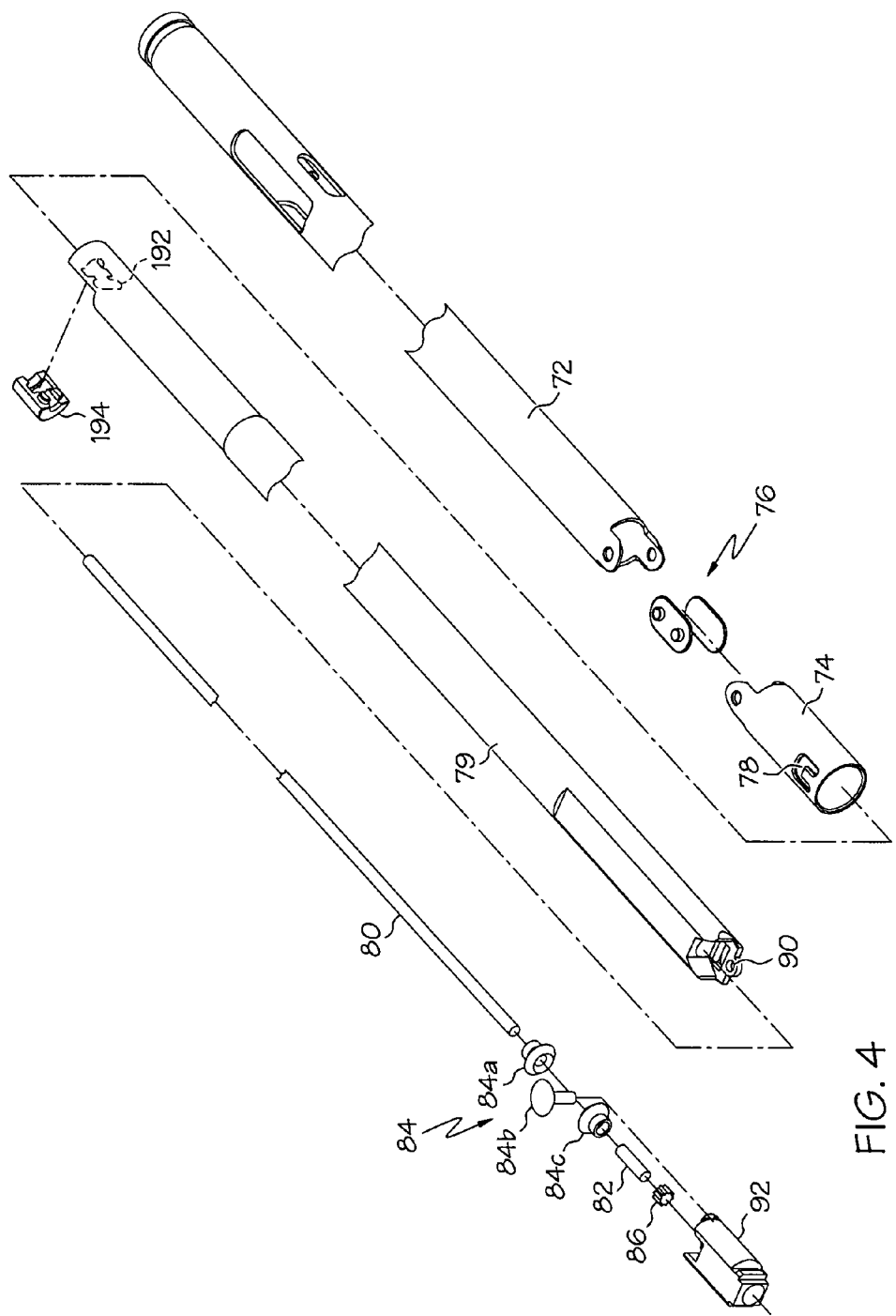
FIGS. 4 and 5 are exploded views of an end effector and shaft of the instrument according to various embodiments of the present invention.
Figure 5:
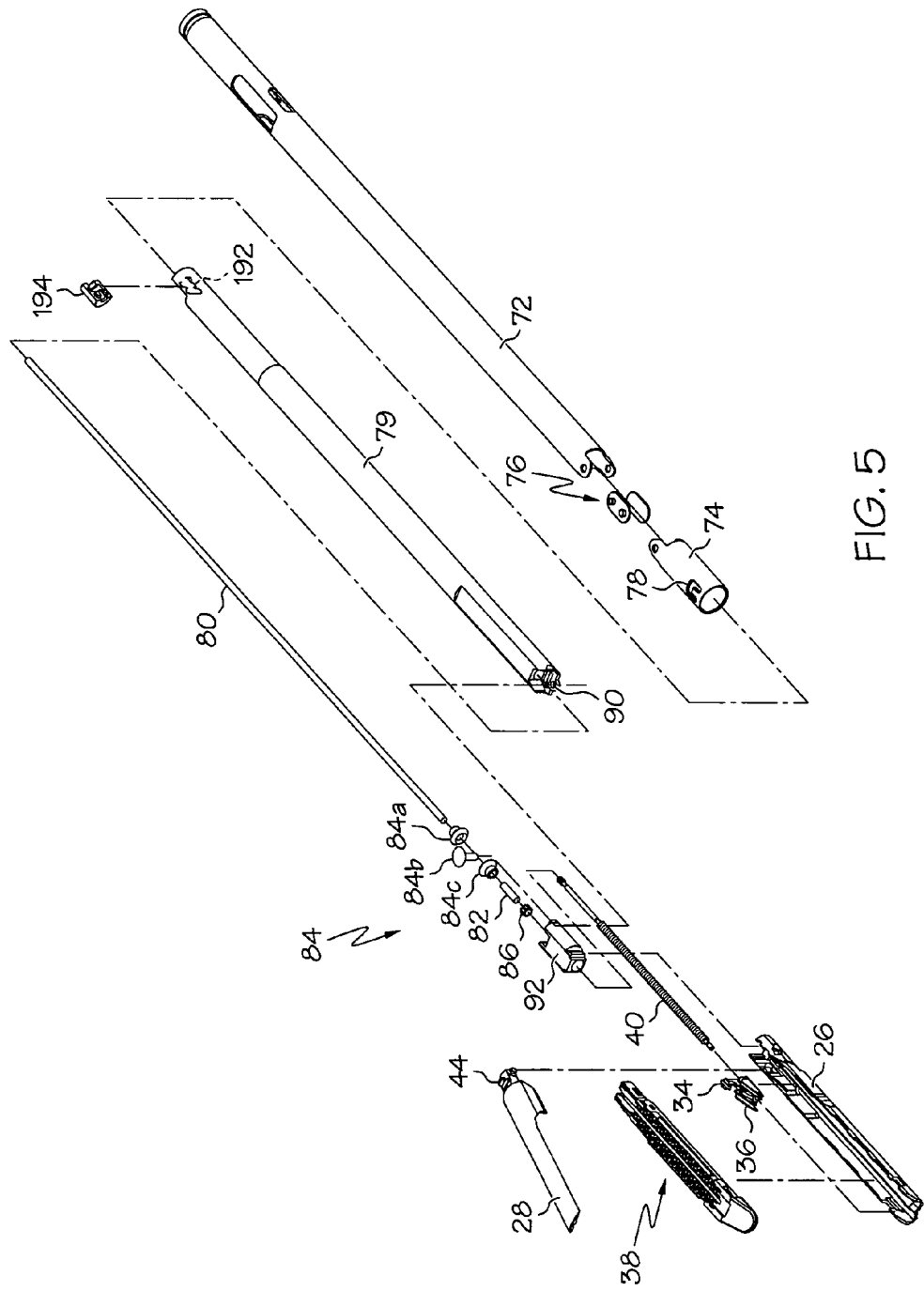
Figure 6:
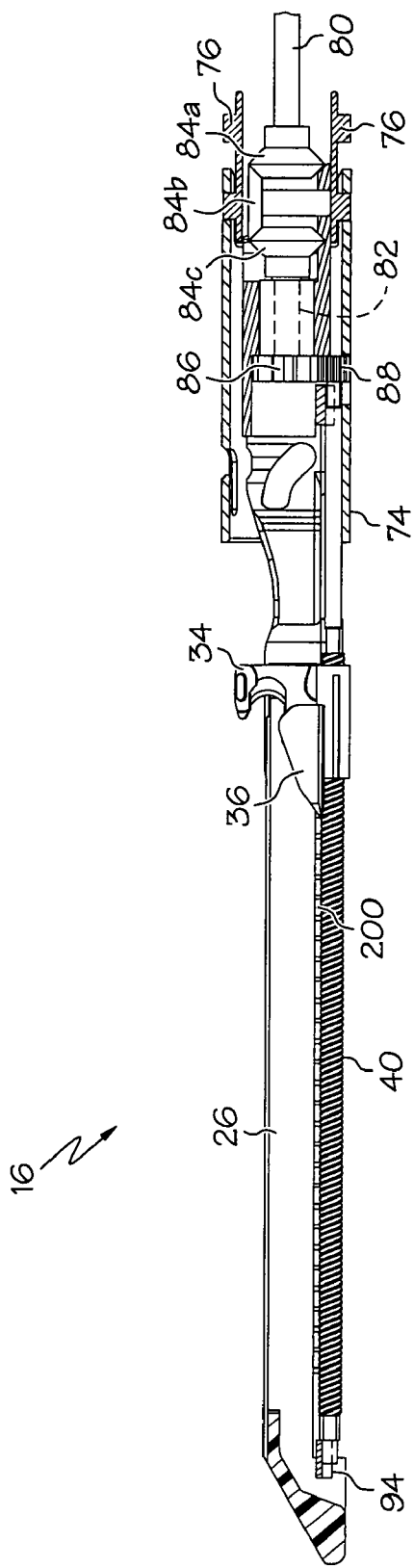
FIG. 6 is a side view of the end effector according to various embodiments of the present invention.
Figure 7:
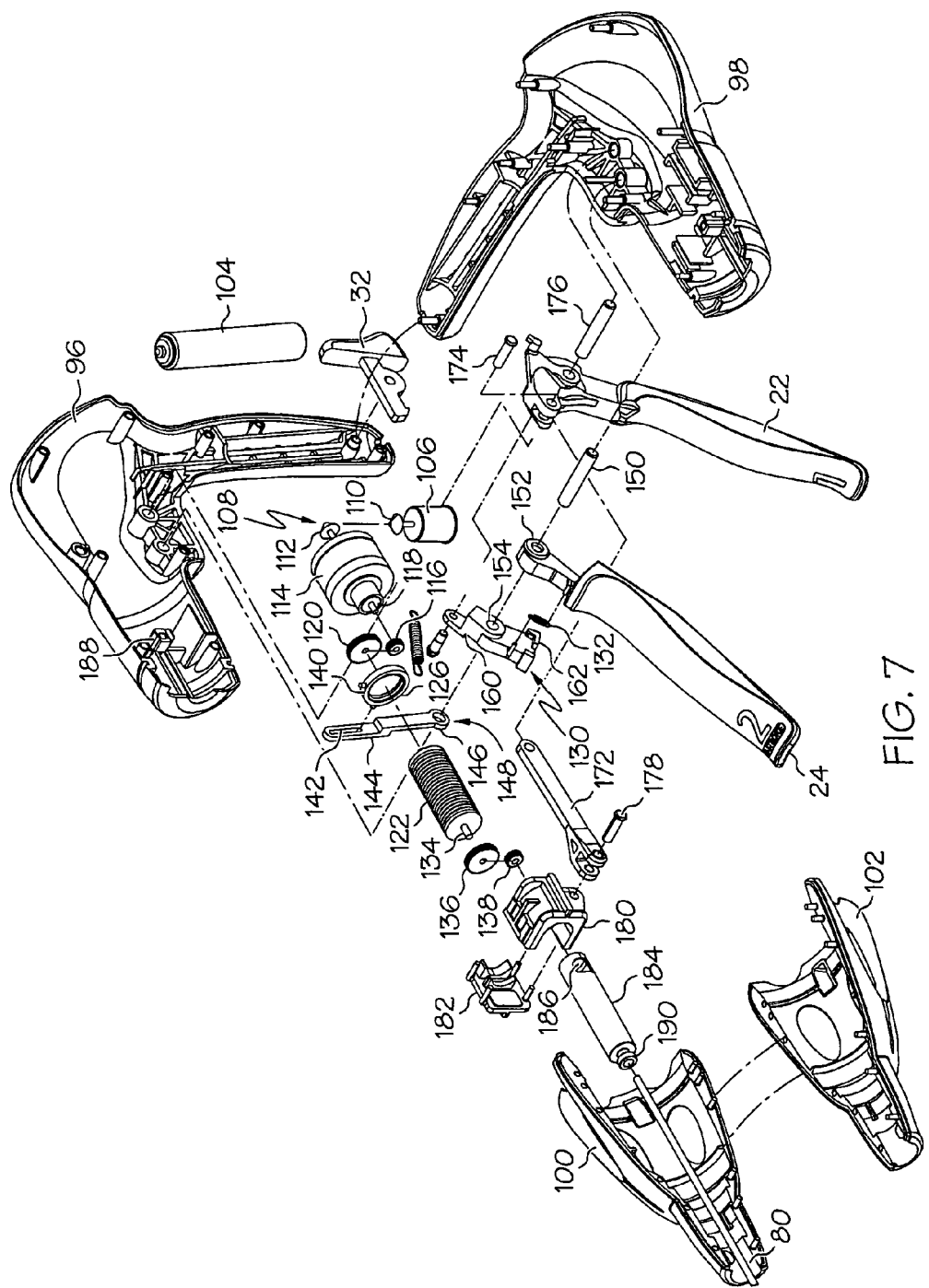
FIG. 7 is an exploded view of the handle of the instrument according to various embodiments of the present invention.

FIGS. 4 and 5 are exploded views and FIG. 6 is a side view of the end effector 16 and shaft 14 according to various embodiments. As shown in the illustrated embodiment, the shaft 14 may include a proximate closure tube 72 and a distal closure tube 74 pivotably linked by a pivot links 76. The distal closure tube 74 includes an opening 78 into which the tab 44 on the anvil 28 is inserted in order to open and close the anvil 28, as further described below. Disposed inside the closure tubes 72, 74 may be a proximate spine tube 79. Disposed inside the proximate spine tube 79 may be a main rotational (or proximate) drive shaft 80 that communicates with a secondary (or distal) drive shaft 82 via a bevel gear assembly 84. The secondary drive shaft 82 is connected to a drive gear 86 that engages a proximate drive gear 88 of the helical screw shaft 40. The vertical bevel gear 84b may sit and pivot in an opening 90 in the distal end of the proximate spine tube 79. A distal spine tube 92 may be used to enclose the secondary drive shaft 82 and the drive gears 86, 88. Collectively, the main drive shaft 80, the secondary drive shaft 82, and the articulation assembly (e.g., the bevel gear assembly 84a-c) are sometimes referred to herein as the "main drive shaft assembly."

A bearing 94, positioned at a distal end of the staple channel 26, receives the helical drive screw 40, allowing the helical drive screw 40 to freely rotate with respect to the channel 26. The helical screw shaft 40 may interface a threaded opening (not shown) of the cutting instrument 34 such that rotation of the shaft 40 causes the cutting instrument 34 to translate distally or proximately (depending on the direction of the rotation) through the staple channel 26. Accordingly, when the main drive shaft 80 is caused to rotate by actuation of the firing trigger 24 (as explained in further detail below), the bevel gear assembly 84a-c causes the secondary drive shaft 82 to rotate, which in turn, because of the engagement of the drive gears 86, 88, causes the helical screw shaft 40 to rotate, which causes the cutting instrument 34 to travel longitudinally along the channel 26 to cut any tissue clamped within the end effector 16. The sled 36 may be made of, for example, plastic, and may have a sloped distal surface. As the sled 36 traverses the channel 26, the sloped distal surface may cam the staple drivers 60 upward, which in turn push up or drive the staples 62 in the staple cartridge 38 through the clamped tissue and against the staple forming undersurface 66 of the anvil 28, thereby stapling the severed tissue. When the cutting instrument 34 is retracted, the cutting instrument 34 and the sled 36 may become disengaged, thereby leaving the sled 36 at the distal end of the channel 26.

FIGS. 7-10 illustrate an exemplary embodiment of a motor-driven endocutter, and in particular the handle 12 thereof, that provides operator-feedback regarding the deployment and loading force of the cutting instrument 34 in the end effector 16. In addition, the embodiment may use power provided by the operator in retracting the firing trigger 24 to power the device (a so-called "power assist" mode). As shown in the illustrated embodiment, the handle 12 includes exterior lower side pieces 96, 98 and exterior upper side pieces 100, 102 that fit together to form, in general, the exterior of the handle 12. A battery 104 may be provided in the pistol grip portion 30 of the handle 12. The battery 64 may be constructed according to any suitable construction or chemistry including, for example, a Li-ion chemistry such as LiCoO2 or LiNiO2, a Nickel Metal Hydride chemistry, etc. The battery 104 powers a motor 106 disposed in an upper portion of the pistol grip portion 30 of the handle 12. According to various embodiments, the motor 106 may be a DC brushed driving motor having a maximum rotation of approximately 5000 to 100,000 RPM. The motor 106 may drive a 90-degree bevel gear assembly 108 comprising a first bevel gear 110 and a second bevel gear 112. The bevel gear assembly 108 may drive a planetary gear assembly 114. The planetary gear assembly 114 may include a pinion gear 116 connected to a drive shaft 118. The pinion gear 116 may drive a mating ring gear 120 that drives a helical gear drum 122 via a drive shaft 124. A ring 126 may be threaded on the helical gear drum 122. Thus, when the motor 106 rotates, the ring 126 is caused to travel along the helical gear drum 122 by means of the interposed bevel gear assembly 108, planetary gear assembly 114 and ring gear 120.

The handle 12 may also include a run motor sensor 128 in communication with the firing trigger 24 to detect when the firing trigger 24 has been drawn in (or "closed") toward the pistol grip portion 30 of the handle 12 by the operator to thereby actuate the cutting/stapling operation by the end effector 16. The sensor 128 may be a proportional sensor such as, for example, a rheostat or variable resistor. When the firing trigger 24 is drawn in, the sensor 128 detects the movement, and sends an electrical signal indicative of the voltage (or power) to be supplied to the motor 106. When the sensor 128 is a variable resistor or the like, the rotation of the motor 106 may be generally proportional to the amount of movement of the firing trigger 24. That is, if the operator only draws or closes the firing trigger 24 in a little bit, the rotation of the motor 106 is relatively low. When the firing trigger 24 is fully drawn in (or in the fully closed position), the rotation of the motor 106 is at its maximum. In other words, the harder the operator pulls on the firing trigger 24, the more voltage is applied to the motor 106, causing a greater rate of rotation. In another embodiment, for example, the control unit (described further below) may output a PWM control signal to the motor 106 based on the input from the sensor 128 in order to control the motor 106.

The handle 12 may include a middle handle piece 130 adjacent to the upper portion of the firing trigger 24. The handle 12 also may comprise a bias spring 132 connected between posts on the middle handle piece 130 and the firing trigger 24. The bias spring 132 may bias the firing trigger 24 to its fully open position. In that way, when the operator releases the firing trigger 24, the bias spring 132 will pull the firing trigger 24 to its open position, thereby removing actuation of the sensor 128, thereby stopping rotation of the motor 106. Moreover, by virtue of the bias spring 132, any time an operator closes the firing trigger 24, the operator will experience resistance to the closing operation, thereby providing the operator with feedback as to the amount of rotation exerted by the motor 106. Further, the operator could stop retracting the firing trigger 24 to thereby remove force from the sensor 128, to thereby stop the motor 106. As such, the operator may stop the deployment of the end effector 16, thereby providing a measure of control of the cutting/fastening operation to the operator.

The distal end of the helical gear drum 122 includes a distal drive shaft 134 that drives a ring gear 136, which mates with a pinion gear 138. The pinion gear 138 is connected to the main drive shaft 80 of the main drive shaft assembly. In that way, rotation of the motor 106 causes the main drive shaft assembly to rotate, which causes actuation of the end effector 16, as described above.

The ring 126 threaded on the helical gear drum 122 may include a post 140 that is disposed within a slot 142 of a slotted arm 144. The slotted arm 144 has an opening 146 its opposite end 148 that receives a pivot pin 150 that is connected between the handle exterior side pieces 96, 98. The pivot pin 150 is also disposed through an opening 152 in the firing trigger 24 and an opening 154 in the middle handle piece 130.

In addition, the handle 12 may include a reverse motor (or end-of-stroke) sensor 156 and a stop motor (or beginning-of-stroke) sensor 158. In various embodiments, the reverse motor sensor 156 may be a normally-open limit switch located at the distal end of the helical gear drum 122 such that the ring 126 threaded on the helical gear drum 122 contacts and closes the reverse motor sensor 156 when the ring 126 reaches the distal end of the helical gear drum 122. The reverse motor sensor 156, when closed, sends a signal to the control unit which sends a signal to the motor 106 to reverse its rotation direction, thereby withdrawing the cutting instrument of the end effector 16 following the cutting operation.

The stop motor sensor 158 may be, for example, a normally-closed limit switch. In various embodiments, it may be located at the proximate end of the helical gear drum 122 so that the ring 126 opens the switch 158 when the ring 126 reaches the proximate end of the helical gear drum 122.

In operation, when an operator of the instrument 10 pulls back the firing trigger 24, the sensor 128 detects the deployment of the firing trigger 24 and sends a signal to the control unit which sends a signal to the motor 106 to cause forward rotation of the motor 106 at, for example, a rate proportional to how hard the operator pulls back the firing trigger 24. The forward rotation of the motor 106 in turn causes the ring gear 120 at the distal end of the planetary gear assembly 114 to rotate, thereby causing the helical gear drum 122 to rotate, causing the ring 126 threaded on the helical gear drum 122 to travel distally along the helical gear drum 122. The rotation of the helical gear drum 122 also drives the main drive shaft assembly as described above, which in turn causes deployment of the cutting instrument 34 in the end effector 16. That is, the cutting instrument 34 and sled 36 are caused to traverse the channel 26 longitudinally, thereby cutting tissue clamped in the end effector 16. Also, the stapling operation of the end effector 16 is caused to happen in embodiments where a stapling-type end effector is used.

By the time the cutting/stapling operation of the end effector 16 is complete, the ring 126 on the helical gear drum 122 will have reached the distal end of the helical gear drum 122, thereby causing the reverse motor sensor 156 to be actuated, which sends a signal to the control unit which sends a signal to the motor 106 to cause the motor 106 to reverse its rotation. This in turn causes the cutting instrument 34 to retract, and also causes the ring 126 on the helical gear drum 122 to move back to the proximate end of the helical gear drum 122.

Figure 8:
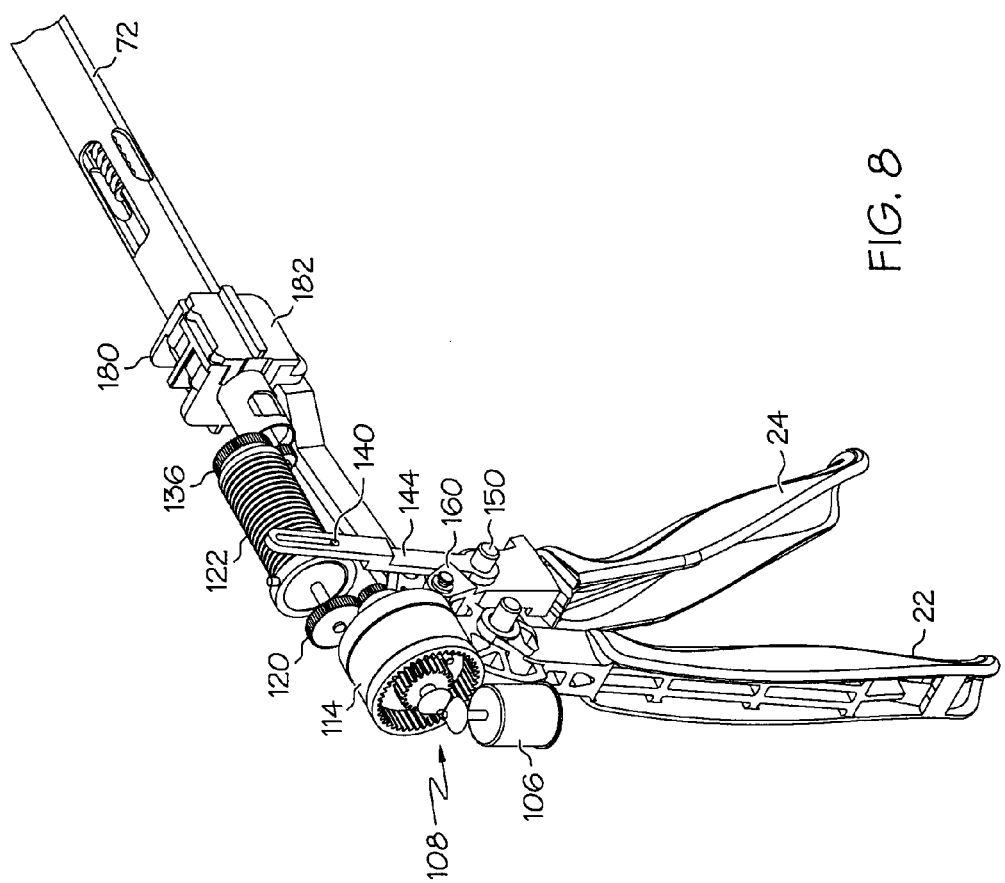
FIGS. 8 and 9 are partial perspective views of the handle according to various embodiments of the present invention.
Figure 9:
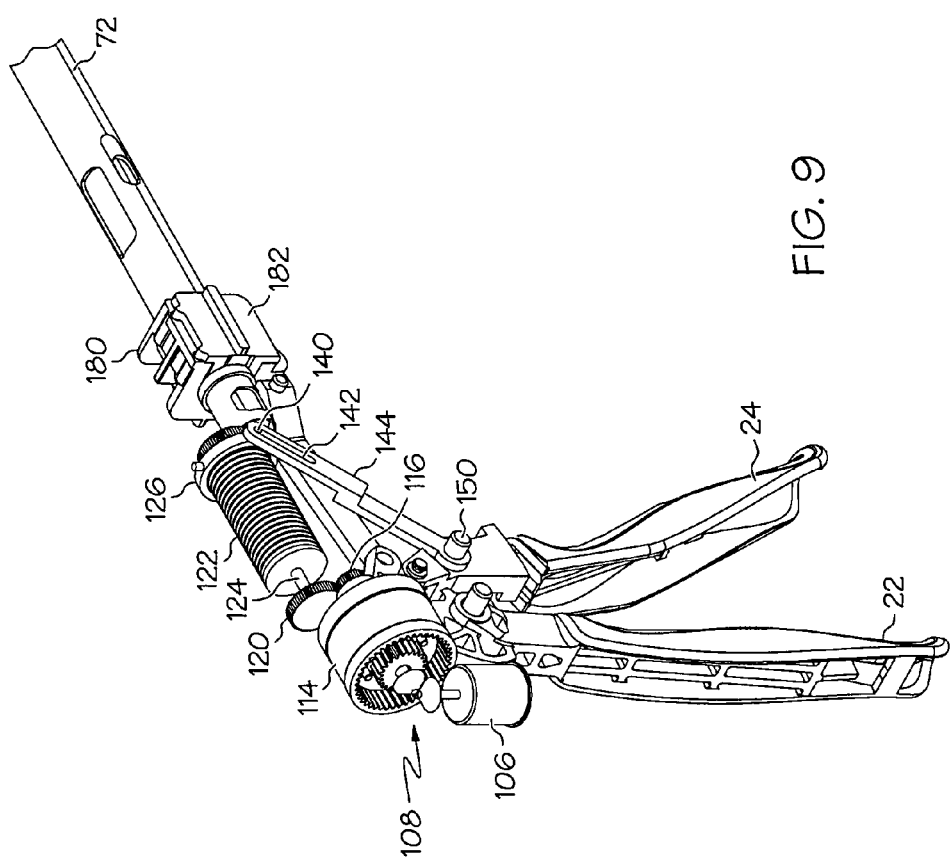
Figure 10:
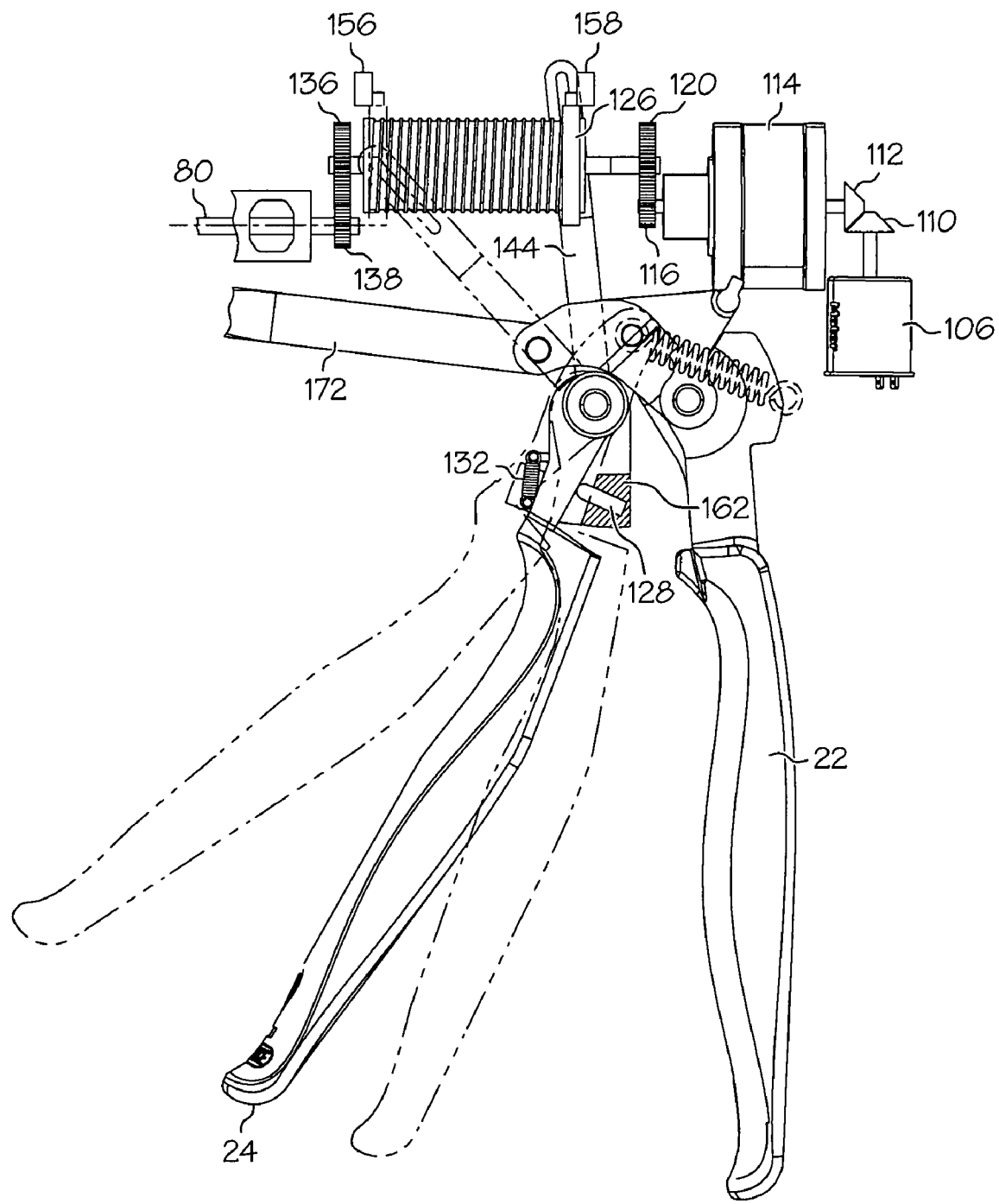
FIG. 10 is a side view of the handle according to various embodiments of the present invention.

The middle handle piece 130 includes a backside shoulder 160 that engages the slotted arm 144 as best shown in FIGS. 8 and 9. The middle handle piece 130 also has a forward motion stop 162 that engages the firing trigger 24. The movement of the slotted arm 144 is controlled, as explained above, by rotation of the motor 106. When the slotted arm 144 rotates CCW as the ring 126 travels from the proximate end of the helical gear drum 122 to the distal end, the middle handle piece 130 will be free to rotate CCW. Thus, as the operator draws in the firing trigger 24, the firing trigger 24 will engage the forward motion stop 162 of the middle handle piece 130, causing the middle handle piece 130 to rotate CCW. Due to the backside shoulder 160 engaging the slotted arm 144, however, the middle handle piece 130 will only be able to rotate CCW as far as the slotted arm 144 permits. In that way, if the motor 106 should stop rotating for some reason, the slotted arm 144 will stop rotating, and the operator will not be able to further draw in the firing trigger 24 because the middle handle piece 130 will not be free to rotate CCW due to the slotted arm 144.

Figure 11:
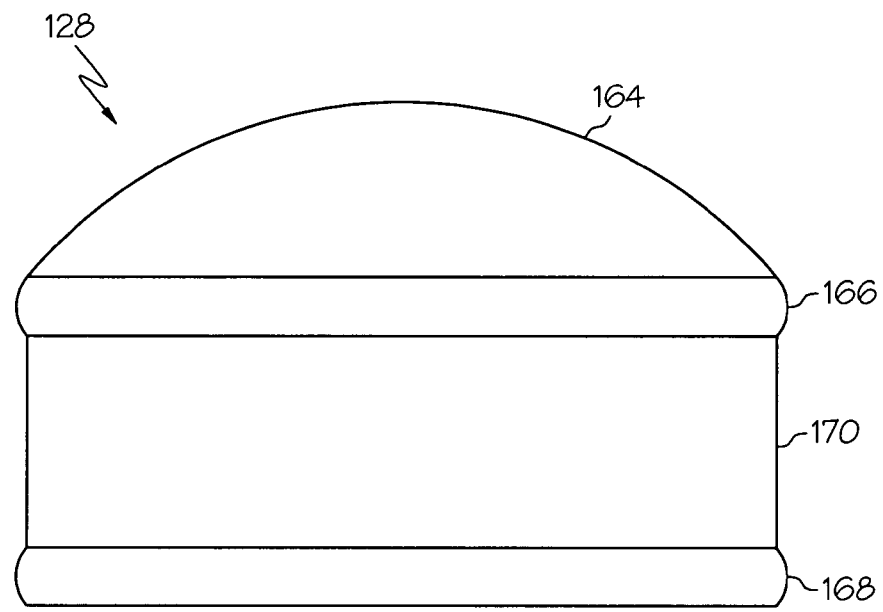
FIGS. 11 and 12 illustrate a proportional sensor that may be used according to various embodiments of the present invention.
Figure 12:
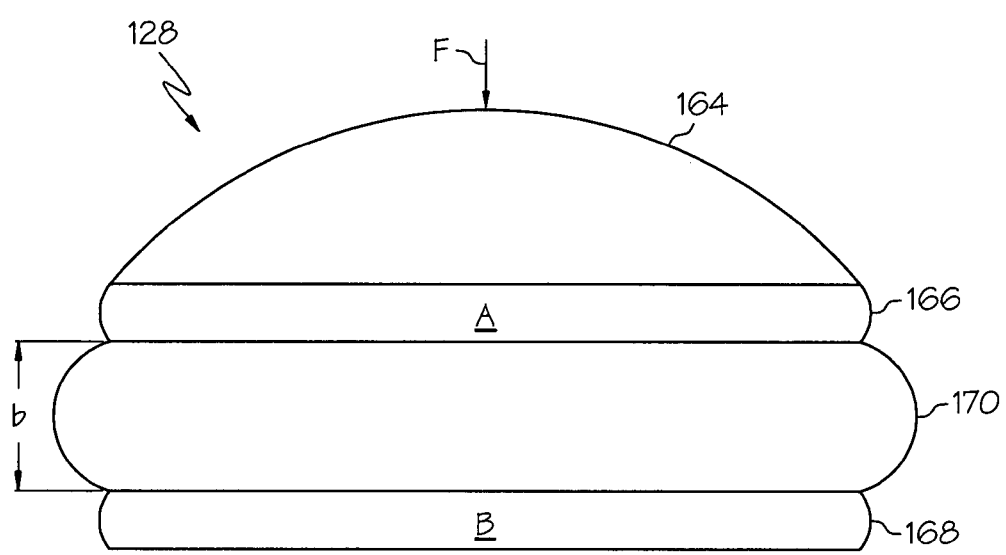

FIGS. 11 and 12 illustrate two states of a variable sensor that may be used as the run motor sensor 128 according to various embodiments of the present invention. The sensor 128 may include a face portion 164, a first electrode (A) 166, a second electrode (B) 168, and a compressible dielectric material 170 (e.g., EAP) between the electrodes 166, 168. The sensor 128 may be positioned such that the face portion 164 contacts the firing trigger 24 when retracted. Accordingly, when the firing trigger 24 is retracted, the dielectric material 170 is compressed, as shown in FIG. 12, such that the electrodes 166, 168 are closer together. Since the distance "b" between the electrodes 166, 168 is directly related to the impedance between the electrodes 166, 168, the greater the distance the more impedance, and the closer the distance the less impedance. In that way, the amount that the dielectric material 170 is compressed due to retraction of the firing trigger 24 (denoted as force "F" in FIG. 12) is proportional to the impedance between the electrodes 166, 168. This impedance provided by the sensor 128 may be used with suitable signal conditioning circuitry to proportionally control the speed of the motor 106, for example.

Components of an exemplary closure system for closing (or clamping) the anvil 28 of the end effector 16 by retracting the closure trigger 22 are also shown in FIGS. 7-10. In the illustrated embodiment, the closure system includes a yoke 172 connected to the closure trigger 22 by a pin 174 that is inserted through aligned openings in both the closure trigger 22 and the yoke 172. A pivot pin 176, about which the closure trigger 22 pivots, is inserted through another opening in the closure trigger 22 which is offset from where the pin 174 is inserted through the closure trigger 22. Thus, retraction of the closure trigger 22 causes the upper part of the closure trigger 22, to which the yoke 172 is attached via the pin 174, to rotate CCW. The distal end of the yoke 172 is connected, via a pin 178, to a first closure bracket 180. The first closure bracket 180 connects to a second closure bracket 182. Collectively, the closure brackets 180, 182 define an opening in which the proximal end of the proximate closure tube 72 (see FIG. 4) is seated and held such that longitudinal movement of the closure brackets 180, 182 causes longitudinal motion by the proximate closure tube 72. The instrument 10 also includes a closure rod 184 disposed inside the proximate closure tube 72. The closure rod 184 may include a window 186 into which a post 188 on one of the handle exterior pieces, such as exterior lower side piece 96 in the illustrated embodiment, is disposed to fixedly connect the closure rod 184 to the handle 12. In that way, the proximate closure tube 72 is capable of moving longitudinally relative to the closure rod 184. The closure rod 184 may also include a distal collar 190 that fits into a cavity 192 in proximate spine tube 79 and is retained therein by a cap 194 (see FIG. 4).

In operation, when the yoke 172 rotates due to retraction of the closure trigger 22, the closure brackets 180, 182 cause the proximate closure tube 72 to move distally (i.e., away from the handle 12 of the instrument 10), which causes the distal closure tube 74 to move distally, which causes the anvil 28 to rotate about the pivot point 42 into the clamped or closed position. When the closure trigger 22 is unlocked from the locked position, the proximate closure tube 72 is caused to slide proximally, which causes the distal closure tube 74 to slide proximally, which, by virtue of the tab 44 being inserted in the opening 78 of the distal closure tube 74, causes the anvil 28 to pivot about the pivot point 42 into the open or unclamped position. In that way, by retracting and locking the closure trigger 22, an operator may clamp tissue between the anvil 28 and channel 26, and may unclamp the tissue following the cutting/stapling operation by unlocking the closure trigger 22 from the locked position.

The control unit (described further below) may receive the outputs from end-of-stroke and beginning-of-stroke sensors 156, 158 and the run-motor sensor 128, and may control the motor 106 based on the inputs. For example, when an operator initially pulls the firing trigger 24 after locking the closure trigger 22, the run-motor sensor 128 is actuated. If the control unit determines that an unspent staple cartridge 38 is present in the end effector 16, as described further below, the control unit may output a control signal to the motor 106 to cause the motor 106 to rotate in the forward direction. When the end effector 16 reaches the end of its stroke, the reverse motor sensor 156 will be activated. The control unit may receive this output from the reverse motor sensor 156 and cause the motor 106 to reverse its rotational direction. When the cutting instrument 34 is fully retracted, the stop motor sensor switch 158 is activated, causing the control unit to stop the motor 106.

According to various embodiments, the instrument 10 may include a transponder in the end effector 16. The transponder may generally be any device suitable for transmitting a wireless signal(s) indicating one or more conditions of the end effector 16. In certain embodiments, for example, wireless signals may be transmitted by the transponder to the control unit responsive to wireless signals received from the control unit. In such embodiments, the wireless signals transmitted by the control unit and the transponder are referred to as "interrogation" and "reply" signals, respectively. The transponder may be in communication with one or more types of sensors (e.g., position sensors, displacement sensors, pressure/load sensors, proximity sensors, etc.) located in the end effector 16 for transducing various end effector conditions such as, for example, a state of the staple cartridge 38 (e.g., fired or unfired) and the respective positions of the anvil 28 (e.g., open or closed) and the sled 36 (e.g., proximal or distal). Placement of sensors to determine such conditions is described in pending U.S. patent application Ser. No. 11/343,439 referenced above, which is incorporated herein. According to various embodiments and as discussed below, the transponder may be a passive device such that its operating power is derived from wireless signals (e.g., interrogation signals). In other embodiments, the transponder may be an active device powered by a self-contained power source (e.g., a battery) disposed within the end effector 16. The transponder and the control circuit may be configured to communicate using any suitable type of wireless signal. According to various embodiments and as discussed below, for example, the transponder and the control circuit may transmit and receive wireless signals using magnetic fields generated by inductive effects. It will be appreciated that the transponder and the control circuit may instead transmit and receive wireless signals using electromagnetic fields (e.g., RF signals, optical signals), or using electric fields generated by capacitive effects, for example. It will further be appreciated that the end effector 16 may include additional transponders, with each transponder having one more dedicated sensors for inputting data thereto.

Figure 13:
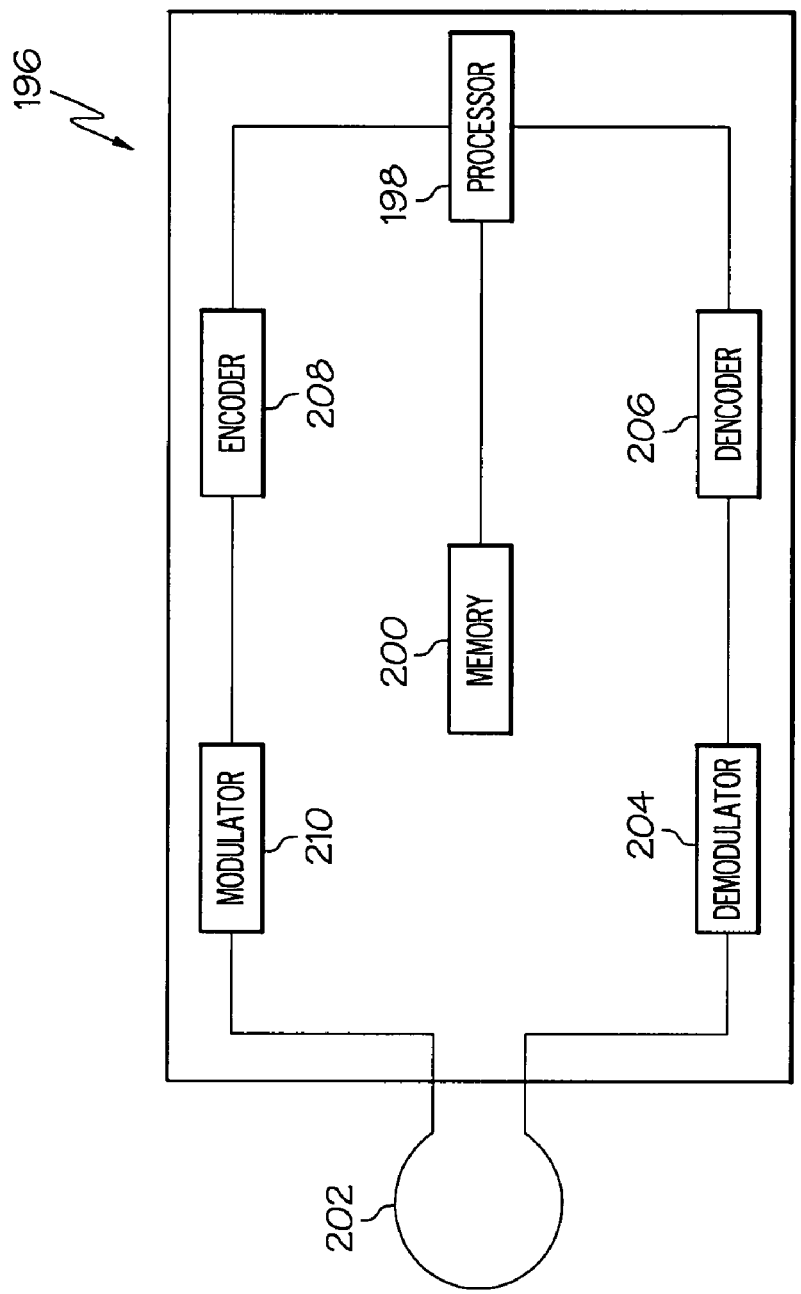
FIG. 13 is a block diagram of a control unit according to various embodiments of the present invention.

FIG. 13 illustrates a block diagram of the control unit 196 according to various embodiments. As shown, the control unit 196 may comprise a processor 198 and one or more memory units 200. The control unit 196 may be powered by the battery 104 or other suitable power source contained within the instrument 10. In certain embodiments, the control unit 196 may further comprise an inductive element 202 (e.g., a coil or antenna) to transmit and receive wireless signals (e.g., interrogation and reply signals) from the transponder via magnetic fields. Signals received by the inductive element 202 may be demodulated by a demodulator 204 and decoded by a decoder 206. By executing instruction code stored in the memory 200, the processor 198 may control various components of the instrument 10, such as the motor 106 and a user display (not shown), based on inputs of the end effector sensors (as indicated by the decoded signals) and inputs received from other various sensor(s) (such as the run-motor sensor 128, the end-of-stroke and beginning-of-stroke sensors 156,158, for example).

Wireless signals output by the control unit 196 may be in the form of alternating magnetic fields emitted by the inductive element 202. The control unit 196 may comprise an encoder 208 for encoding data to be transmitted to the transponder and a modulator 210 for modulating the magnetic field based on the encoded data using a suitable modulation scheme. The control unit 196 may communicate with the transponder using any suitable wireless communication protocol and any suitable frequency (e.g., an ISM band or other RF band). Also, the control unit 196 may transmit signals at a different frequency range than the frequency range of the reply signals received from the transponder. Additionally, although only one antenna (inductive element 202) is shown in FIG. 13, in other embodiments the control unit 196 may have separate receiving and transmitting antennas.

According to various embodiments, the control unit 196 may comprise a microcontroller, a microprocessor, a field programmable gate array (FPGA), one or more other types of integrated circuits (e.g., RF receivers and PWM controllers), and/or discrete passive components. The control unit 196 may also be embodied as system-on-chip (SoC) or a system-in-package (SIP), for example.

Figure 14:
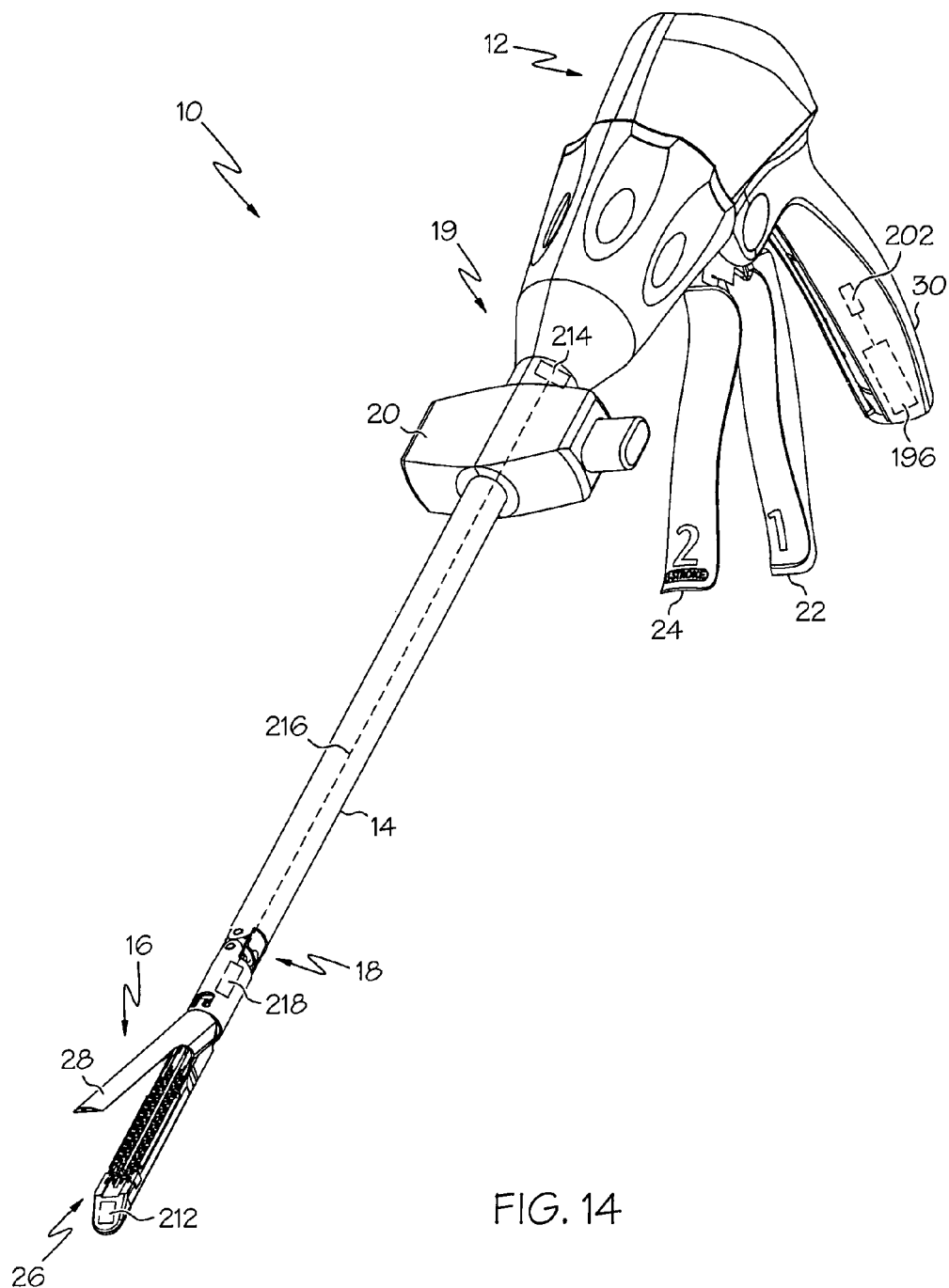
FIGS. 14-16 and FIG. 26 are perspective views of a surgical instrument according to various embodiments of the present invention.

As shown in FIG. 14, the control unit 196 may be housed in the handle 12 of the instrument 10 and the transponder 212 may be located in the end effector 16. To transmit signals to the transponder 212 and receive signals therefrom, the inductive element 202 of the control unit 196 may be inductively coupled to a secondary inductive element (e.g., a coil) 214 positioned in the shaft 14 distally from the rotation joint 19.

The secondary inductive element 214 is preferably electrically insulated from the conductive shaft 14.

The secondary inductive element 214 may be connected by an electrically conductive, insulated wire 216 to a distal inductive element (e.g., a coil) 218 located near the end effector 16, and preferably distally located relative to the articulation pivot 18. The wire 216 may be made of an electrically conductive polymer and/or metal (e.g., copper) and may be sufficiently flexible so that it could pass though the articulation pivot 18 and not be damaged by articulation. The distal inductive element 218 may be inductively coupled to the transponder 212 in, for example, the staple cartridge 38 of the end effector 16. The transponder 212, as described in more detail below, may include an antenna (or coil) for inductively coupling to the distal coil 218, as well as associated circuitry for transmitting and receiving wireless signals.

In certain embodiments, the transponder 212 may be passively powered by magnetic fields emitted by the distal inductive element 218. Once sufficiently powered, the transponder 212 may transmit and/or receive data (e.g., by modulating the magnetic fields) to the control unit 196 in the handle 12 via (i) the inductive coupling between the transponder 212 and the distal inductive element 218, (ii) the wire 216, and (iii) the inductive coupling between the secondary inductive element 214 and the control unit 196. The control unit 196 may thus communicate with the transponder 212 in the end effector 16 without a hardwired connection through complex mechanical joints like the rotating joint 19 and/or without a hardwired connection from the shaft 14 to the end effector 16, places where it may be difficult to maintain such connections. In addition, because the distances between the inductive elements (e.g., the spacing between (i) the transponder 212 and the distal inductive element 218, and (ii) the secondary inductive element 214 and the control unit 196) are fixed and known, the couplings could be optimized for inductive energy transfer. Also, the distances could be relatively short so that relatively low power signals could be used to thereby minimize interference with other systems in the use environment of the instrument 10.

Figure 15:
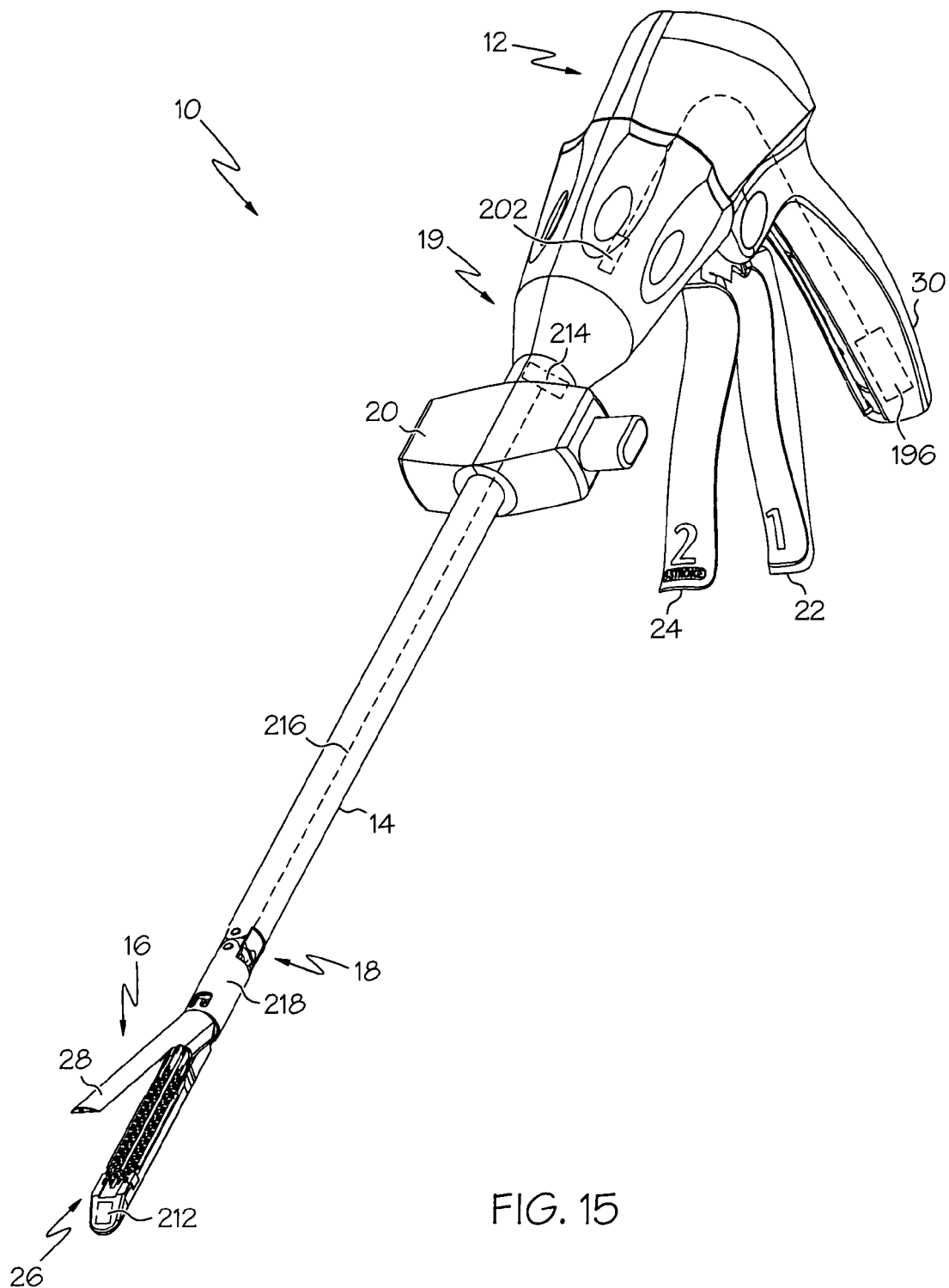

In the embodiment of FIG. 14, the inductive element 202 of the control unit 196 is located relatively near to the control unit 196. According to other embodiments, as shown in FIG. 15, the inductive element 202 of the control unit 196 may be positioned closer to the rotating joint 19 to that it is closer to the secondary inductive element 214, thereby reducing the distance of the inductive coupling in such an embodiment. Alternatively, the control unit 196 (and hence the inductive element 202) could be positioned closer to the secondary inductive element 214 to reduce the spacing.

Figure 16:
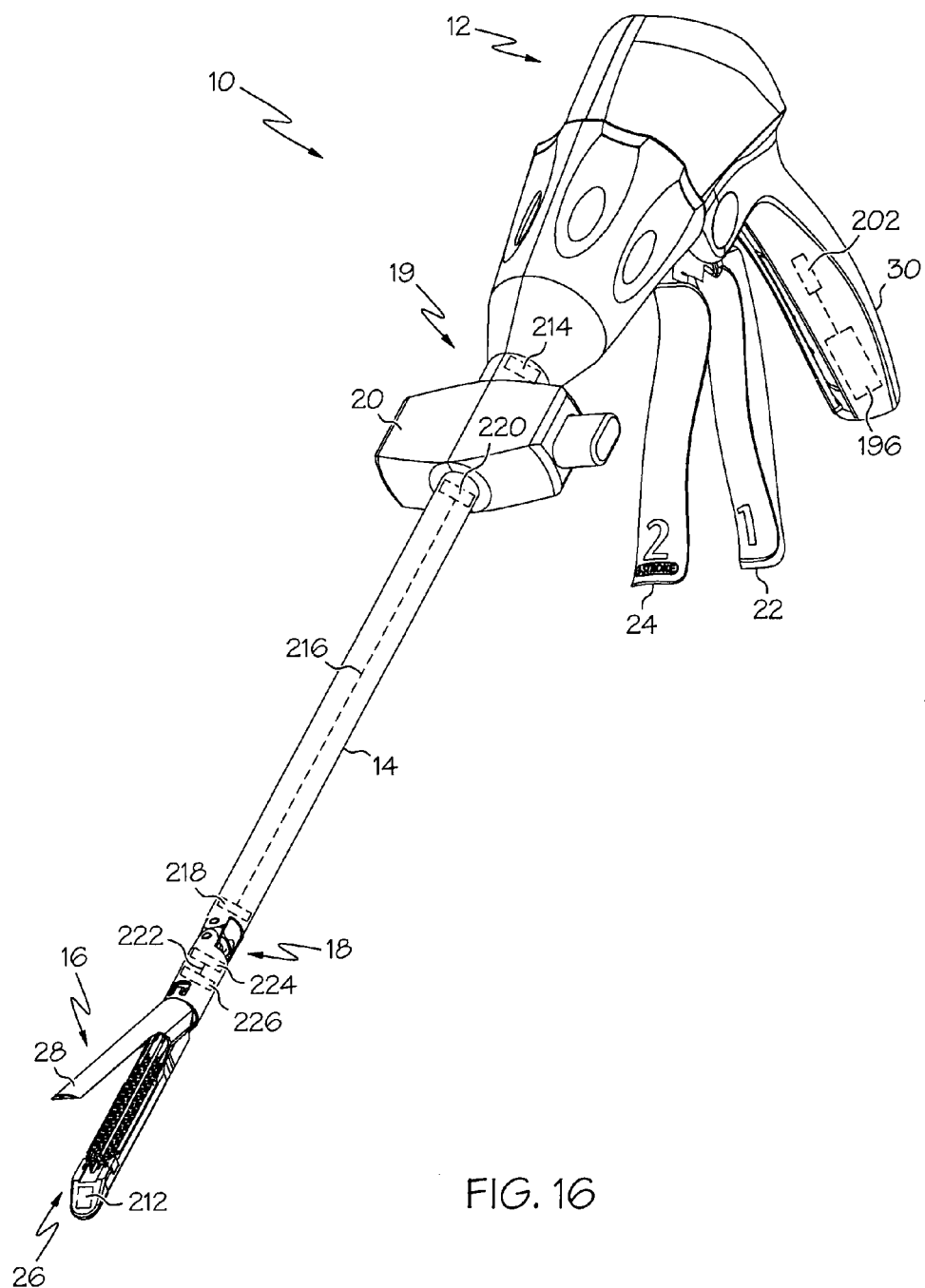

In other embodiments, more or fewer than two inductive couplings may be used. For example, in some embodiments, the surgical instrument 10 may use a single inductive coupling between the control unit 196 in the handle 12 and the transponder 212 in the end effector 16, thereby eliminating the inductive elements 214, 218 and the wire 216. Of course, in such an embodiment, stronger signals may be required due to the greater distance between the control unit 196 in the handle 12 and the transponder 212 in the end effector 16. Also, more than two inductive couplings could be used. For example, if the surgical instrument 10 had numerous complex mechanical joints where it would be difficult to maintain a hardwired connection, inductive couplings could be used to span each such joint. For example, inductive couplings could be used on both sides of the rotary joint 19 and both sides of the articulation pivot 18, with an inductive element 220 on the distal side of the rotary joint 19 connected by the wire 216 to the inductive element 218 of the proximate side of the articulation pivot, and a wire 222 connecting inductive elements 224, 226 on the distal side of the articulation pivot 18 as shown in FIG. 16. In this embodiment, the inductive element 226 may communicate with the transponder 212.

In the above-described embodiments, each of the inductive elements 202, 214, 218, 224, 226 may or may not include ferrite cores. Additionally, the inductive elements 214, 218, 224, 226 are also preferably insulated from the electrically conductive outer shaft (or frame) of the instrument 10 (e.g., the closure tubes 72, 74), and the wires 216, 222 are also preferably insulated from the outer shaft 14.

Figure 17:
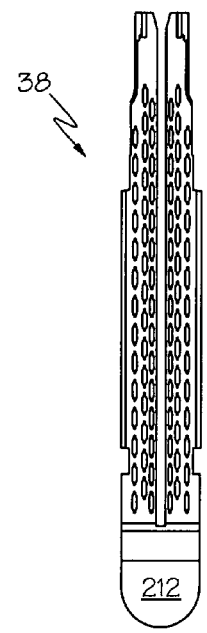
FIG. 17 is a bottom view of a portion of a staple cartridge according to various embodiments.

FIG. 17 is a bottom view of a portion of the staple cartridge 38 including the transponder 212 according to various embodiments. As shown, the transponder 212 may be held or embedded in the staple cartridge 38 at its distal end using a suitable bonding material, such as epoxy.

Figure 18:
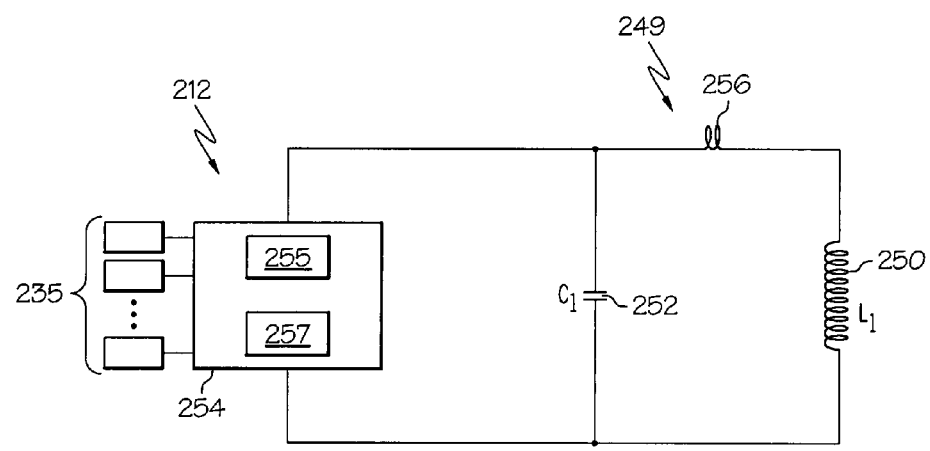
FIGS. 18 and 20 are circuit diagrams of a transponder according to various embodiments.

FIG. 18 illustrates a circuit diagram of the transponder 212 according to various embodiments. As shown, the transponder 212 may include a resonant circuit 249 comprising an inductive element 250 (e.g., a coil or antenna) and a capacitor 252. The transponder 212 may further include a microchip 254 coupled to the resonant circuit 249. In certain embodiments, the microchip 254 may be, for example, an RFID device containing circuitry for enabling communication with the control unit 196 via the inductive element 250 of the resonant circuit 249. The microchip 254 may include at least one data input for receiving data in the form of discrete or analog signals from the sensors 235 disposed in the end effector 16. As discussed above, the sensors 235 may include, for example, position sensors, displacement sensors, pressure/load sensors, proximity sensors for sensing various end effector conditions. The microchip 254 also may include one or more dynamic memory devices 255 (e.g., flash memory devices) for storing data transmitted from, for example, the control unit 196. The microchip 254 may further include one or more non-dynamic memory devices 257 (e.g., write-once memory devices) for storing static data, such as, for example, a staple cartridge identification number, manufacturer information, and information pertaining to physical characteristics of the staple cartridge 38.

In response to alternating magnetic fields emitted by the distal inductive element 218, the resonant circuit 249 of the transponder 212 is caused to resonate, thereby causing an alternating input voltage to be applied to the microchip 254. The resonant circuit 249 may have a resonant frequency given by $$f_r = \frac{1}{2\pi\sqrt{L_1 C_1}},$$

where $L_1$ is the inductance value of the inductive element 250 and $C_1$ is the capacitance value of the capacitor 252. The values of $L_1$ and $C_1$ may be selected such that the resonant frequency of the circuit 249 is equal or nearly equal to the frequency of magnetic field transmitted by the distal inductive element 218. The circuitry of the microchip 254 may include a rectifying circuitry (not shown) for rectifying and conditioning the alternating input voltage to provide a DC voltage sufficient to power the microchip 254. Once powered, the microchip 254 may selectively load the inductive element 250 based on data received from the sensors 235 and the data stored in the memory devices 255, 257, thus modulating the magnetic fields coupling the distal inductive element 218 and the inductive element 250. The modulation of the magnetic field modulates the voltage across the distal inductive element 218, which in turn modulates the voltage across the inductive element 202 of the control unit 196. The control unit 196 may demodulate and decode the voltage signal across the inductive element 202 to extract data communicated by the microchip 254. The control unit 196 may process the data to verify, among other things, that the staple cartridge 38 is compatible with the instrument 10 and that end effector conditions are suitable for conducting a firing operation. Subsequent to verification of the data, the control unit 196 may enable a firing operation.

According to various embodiments, the resonant circuit 249 may further include a fuse 256 connected in series with the inductive element 250. When the fuse 256 is closed (e.g., conductive), the inductive element 250 is electrically coupled to the resonant circuit 249, thus enabling the transponder 212 to function as described above in response to an alternating magnetic field emitted by the distal inductive element 218. The closed state of the fuse 256 thus corresponds to an enabled state of the transponder 212. When the fuse 256 is opened (e.g., non-conductive), the inductive element 250 is electrically disconnected from the resonant circuit 249, thus preventing the resonant circuit 249 from generating the voltage necessary to operate the microchip 254. The open state of the fuse 256 thus corresponds to a disabled state of the transponder 212. The placement of the fuse 256 in FIG. 18 is shown by way of example only, and it will be appreciated that the fuse 256 may be connected in any manner such that the transponder 212 is disabled when the fuse 256 is opened.

According to various embodiments, the fuse 256 may be actuated (e.g., transitioned from closed to opened) substantially simultaneously with a firing operation of the instrument 10. For example, the fuse 256 may be actuated immediately before, during, or immediately after a firing operation. Actuation of the fuse 256 thus transitions the transponder 212 from the enabled state to the disabled state. Accordingly, if an attempt is made to reuse the staple cartridge 38, the transponder 212 will be unable to communicate data in response to a wireless signal transmitted by the distal inductive element 218. Based upon the absence of this data, the control unit 196 may determine that the transponder 212 is in a disabled state indicative of the fired state of the staple cartridge 38 and prevent a firing operation from being enabled. Thus, actuation of the fuse 256 prevents reuse of a staple cartridge 38 when the staple cartridge 38 is in the fired state.

Figure 19:
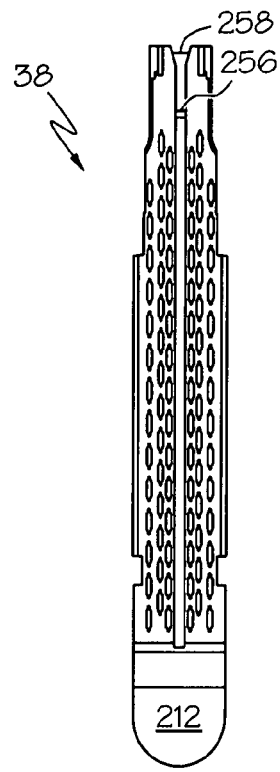
FIG. 19 is a bottom view of a portion of a staple cartridge according to various embodiments.

In certain embodiments, the fuse 256 may be a mechanically-actuated fuse that is opened in response to movement of the cutting instrument 34 when actuated, for example. As shown in FIG. 19, for example, the fuse 256 may include a section of wire extending transversely across a longitudinal slot 258 of the staple cartridge 38 through which the cutting instrument 34 passes during a firing operation. When the instrument 10 is fired, the distal movement of the cutting instrument 34 severs the fuse 256, thus transitioning the transponder 212 to the disabled state so that it cannot be reused.

According to other embodiments, the fuse 256 may be an electrically-actuated fuse. For example, subsequent to receiving data from the transponder 212 and verifying that the end effector 16 is in a condition to be fired, the control unit 196 may transmit a wireless signal to the transponder 212 such that the resulting current flow through fuse 256 is sufficient to cause the fuse 256 to open. It will be appreciated that the strength of the wireless signal needed to open the fuse 256 may be different in amplitude, frequency, and duration than that used to communicate with the transponder 212. Additionally, it will be appreciated that other electrically-actuated components may be used instead of an electrically-actuated fuse to disable the transponder 212. For example, the control unit 196 may transmit a wireless signal to the transponder 212 such that resulting voltage developed across the resonant circuit 256 sufficiently exceeds the voltage rating of the capacitor 252 and/or circuitry of the microchip 254 to cause their destruction.

As an alternative to using an electrically-actuated fuse, the fuse 256 may instead be a thermally-actuated fuse (e.g., a thermal cutoff fuse) that is caused to open in response to heat generated by the flow of excessive current therethrough.

Figure 20:
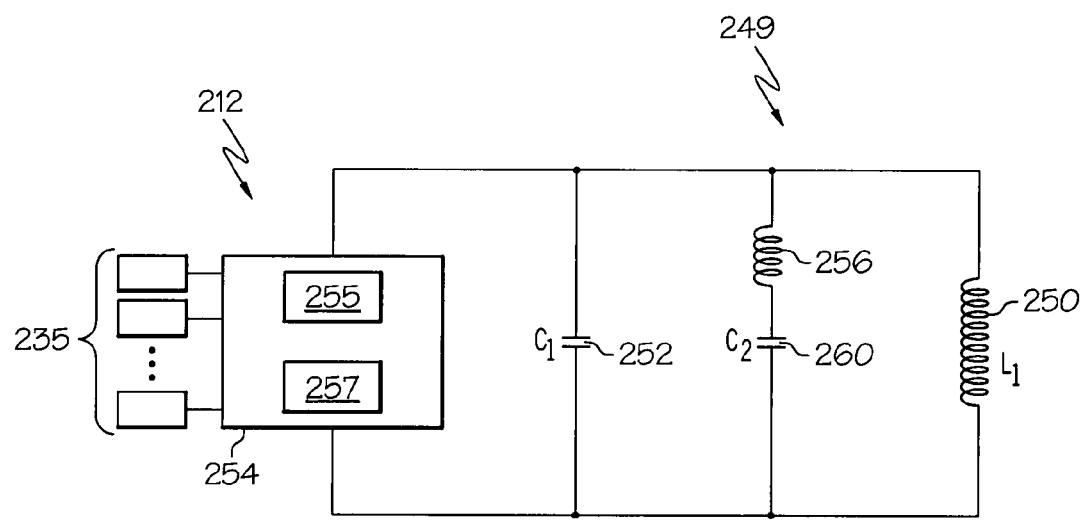

In certain cases, it may be desirable to communicate with the transponder 212 when the staple cartridge 38 is in the fired state. In such cases, it is not possible to entirely disable the transponder 212 as described in the embodiments above. FIG. 20 illustrates a circuit diagram of the transponder 212 according to various embodiments for enabling wireless communication with the control unit 196 when the staple cartridge 38 is in the fired state. As shown, the resonant circuit 249 of the transponder 212 may include a second capacitor 260 in parallel with the capacitor 252. The fuse 256 may be connected in series with the second capacitor 260 such that the resonant frequency of the resonant circuit 249 is determined by the open/closed state of the fuse 256. In particular, when the fuse 256 is closed, the resonant frequency is given by $$f_r = \frac{1}{2\pi\sqrt{L_1(C_1 + C_2)}},$$

where $C_2$ is the capacitance value of the second capacitor 260. The closed state of the fuse 256 thus corresponds to a first resonant state of the transponder 212. When the fuse 256 is opened, the resonant frequency is given by $$f_r = \frac{1}{2\pi\sqrt{L_1 C_1}}.$$

The open state of the fuse 256 thus corresponds to a second resonant state of the transponder 212. As described in the above embodiments, the fuse 256 may be mechanically, electrically or thermally actuated substantially simultaneously with a firing operation. The control unit 196 may be configured to determine the resonant state of the transponder 212 (and thus the unfired/fired state of the staple cartridge 38) by discriminating between the two resonant frequencies. Advantageously, because the resonant circuit 256 (and thus the microchip 254) continue to operate after the fuse 256 is opened, the control unit 196 may continue to receive data from the transponder 212. It will be appreciated that the placement of the fuse 256 and use of the second capacitor 260 to alter the resonant frequency is provided by way of example only. In other embodiments, for example, the fuse 256 may be connected such that the inductive value of the inductive element 250 is changed when the fuse 256 is opened (e.g., by connecting the fuse 256 such that a portion of the inductive element 250 is short-circuited when the fuse 256 is closed).

Figure 21:
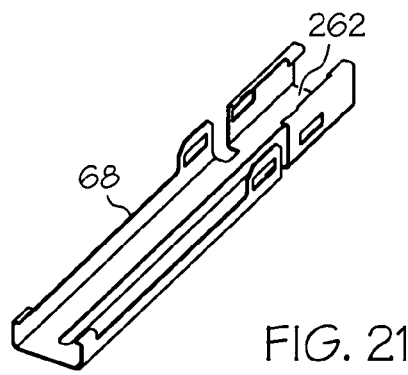
FIG. 21 is a perspective view of a staple cartridge tray according to various embodiments.

According to various embodiments, a switch may be used as an alternative to the fuse 256 for effecting the transition between transponder states. For example, as shown in FIG. 21, the staple cartridge tray 68 of the staple cartridge 38 may include a switch 262 (e.g., a normally-open limit switch) located at its proximal end. The switch 262 may be mounted such that when the sled 36 is present in the unfired position, the sled 36 maintains the switch 262 in a closed (e.g., conductive) state. When the sled 36 is driven from the unfired position to the fired position during a firing operation, the switch 262 transitions to an open (e.g., non-conductive state), thus effecting a transition in the state of the transponder 212 as described above. It will be appreciated that in other embodiments the switch 262 may be a normally-closed switch mounted at the distal end of the staple cartridge tray 68 such that the switch 262 is caused to open when the sled 36 is present in the fired position. It will further be appreciated that the switch 262 may be located at the proximal or distal ends of the staple cartridge 38 and mounted such that it may be suitably actuated by the sled 36 when present in the unfired and fired positions, respectively.

As an alternative to connecting the mechanically-actuated fuse 256 or the switch 262 to disable/alter the resonant circuit 249, these components may instead be connected to data inputs of the microchip 254. In this way, the open/closed states of the mechanically-actuated fuse 256 or the switch 262 may be transmitted to the control unit 196 in the same manner as the data corresponding to other end effector conditions.

As an alternative to the fuse 256 and the switch 262, embodiments of the present invention may instead utilize alterable data values in a dynamic memory device 255 of the transponder 212. For example, the dynamic memory device 255 may store a first data value (e.g., a data bit having a value of 1) corresponding to a first data state of the transponder 212. The first data value may be written to the dynamic memory device 255 during the manufacture of the staple cartridge 38, for example. The first data state may thus be indicative of the unfired state of the staple cartridge 38. Based on a determination of the first data state of the transponder 212, the control unit 196 may enable operation of the instrument 10 if the end effector conditions are otherwise suitable for conducting a firing operation. Substantially simultaneously with the firing operation, the control unit 196 may transmit a wireless signal to the transponder 212 containing a second data value (e.g., a data bit having a value of 0). The second data value may be stored to the dynamic memory device 255 such that the first data value is overwritten, thus transitioning the transponder 212 from the first data state to a second data state. The second data state may thus be indicative of the fired state of the staple cartridge 38. If an attempt is made to reuse the staple cartridge 38, the control unit 196 may determine that the transponder 212 is in the second data state and prevent a firing operation from being enabled.

Figure 22:
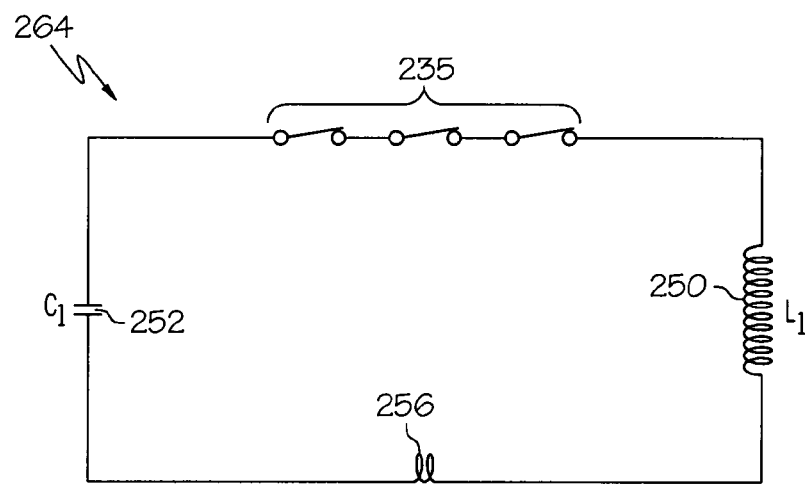
FIGS. 22 and 23 are circuit diagrams of a transponder according to various embodiments.

Although the transponders 212 in the above-described embodiments includes a microchip 254 for wirelessly communicating data stored in memory devices 235, 237 and data input from the sensors 235, in other embodiments the transponder may not include a microchip 254. For example, FIG. 22 illustrates a "chipless" transponder 264 in the form of a resonant circuit having components similar to those of the resonant circuit 249, such as an inductive element 250, a capacitor 252, and a fuse 256. Additionally, the transponder 264 may include one or more sensors 235 connected in series with the components 250, 252, 256. In certain embodiments and as shown, each sensor 235 may be a limit switch (e.g., a normally open or a normally closed limit switch) mounted in the end effector 16 for sensing a corresponding end effector condition (e.g., a position of the anvil 28, a position of the sled 36, etc.). In such embodiments, each limit switch 235 may be in a closed (e.g., conductive) state when its sensed condition is compatible with a firing operation, thus establishing electrical continuity through the resonant circuit.

When each switch 235 and the fuse 256 is in the closed state, the resonant circuit will be caused to resonate at a frequency $f_r$ responsive to a magnetic field emitted by the distal inductive element 218. The closed states of the fuse 256 and the switches 235 thus correspond to an enabled state of the transponder 264 that is indicative of, among other things, the unfired state of the staple cartridge 38. The control unit 196 may sense the resonance (e.g., by sensing magnetic field loading caused by the resonant circuit) to determine the enabled state, at which time the control unit 196 may enable operation of the instrument 10. Substantially simultaneously with the actuation of the cutting instrument 34, the fuse 256 may be mechanically, electronically or thermally actuated as described above, thus transitioning the transponder 264 to a disabled state indicative of the fired state of the staple cartridge 38. If a subsequent firing operation is attempted without replacing the staple cartridge 38, the control unit 196 may determine the disabled state based on the absence of a sensed resonance in response to an emitted magnetic field, in which case the control unit 196 prevents the firing operation from being performed.

Figure 23:
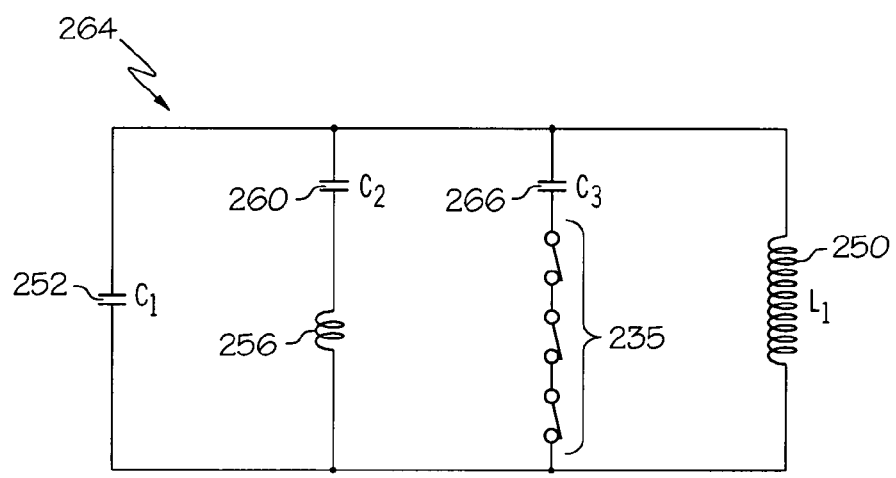

FIG. 23 illustrates another embodiment of a chipless transponder 264 in the form of a resonant circuit including an inductive element 250, a first capacitor 252, a second capacitor 260, and a fuse 256 connected in series with the second capacitor 260. The fuse 256 may be mechanically, electronically or thermally actuated substantially simultaneously with a firing operation, as in above-described embodiments. The transponder 264 may additionally include one or more sensors 235 (e.g., limit switches) connected in series with a third capacitor 266 of the resonant circuit. Accordingly, when each switch 235 and the fuse 256 are in the closed state, the resonant circuit will be caused to resonate at a frequency $$f_{r1} = \frac{1}{2\pi\sqrt{L_1(C_1 + C_2 + C_3)}}$$

responsive to a magnetic field emitted by the distal inductive element 218. When one of the switches 235 is opened and the fuse 256 is closed, the resonant frequency will be $$f_{r2} = \frac{1}{2\pi\sqrt{L_1(C_1 + C_2)}},$$

and when each of the switches 235 is closed and the fuse 256 is opened, the resonant frequency will be $$f_{r3} = \frac{1}{2\pi\sqrt{L_1(C_1 + C_3)}}.$$

When the switches 235 and the fuse 256 are opened, the resonant frequency will be $$f_{r4} = \frac{1}{2\pi\sqrt{L_1 C_1}}.$$

The closed states of the fuse 256 and the switches 235 correspond to a first resonant state (e.g., resonant frequency $f_{r1}$) of the transponder 264, and the open state of the fuse 256 corresponds to a second resonant state (e.g., either of resonant frequencies $f_{r3}$ or $f_{r4}$). The capacitance values $C_1$, $C_2$ and $C_3$ may be selected such that the resonant frequencies $f_{r1}$, $f_{r2}$, $f_{r3}$ and $f_{r4}$ are different. The control unit 196 may be configured to discriminate between resonant frequencies to determine the first or second state of the transponder 266 (and thus the unfired or fired state of the staple cartridge 38), and to enable or prevent operation of the instrument 10 accordingly. The control unit 196 may further be configured to determine a third state of the transponder 264 corresponding the closed state of the fuse 256 and an open state of any of the switches 235. In this case, the control unit 196 may operate to prevent a firing operation until the end effector condition(s) causing the open switch(es) 235 is resolved.

Figure 24:
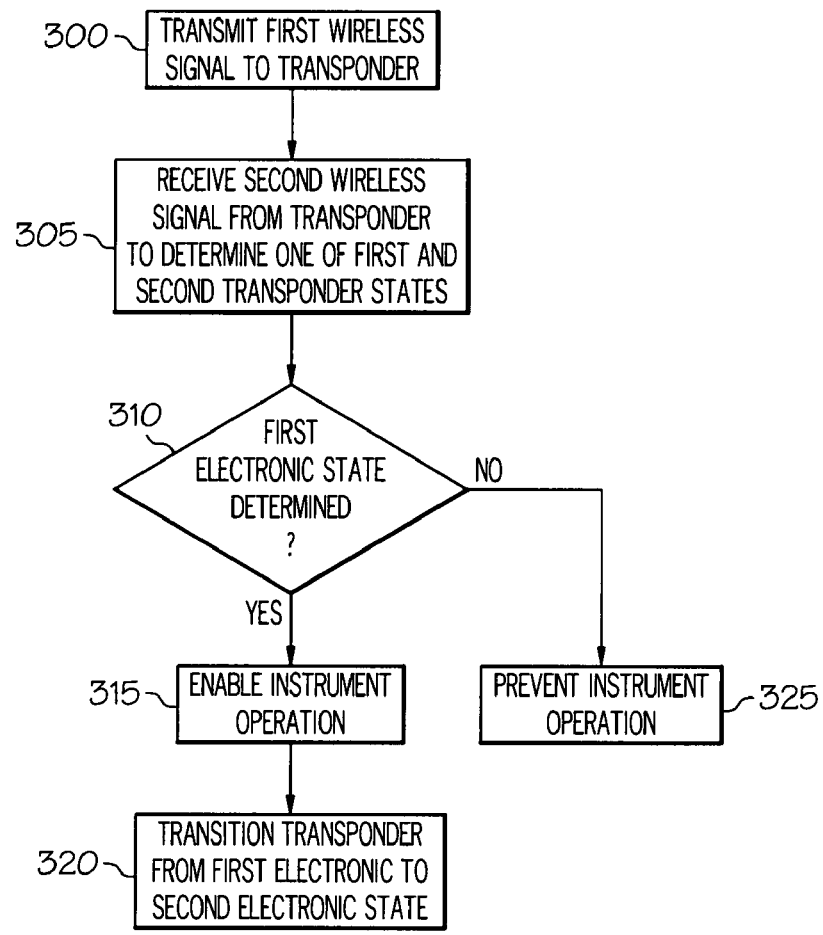
FIG. 24 is a flow diagram of a method of preventing reuse of a staple cartridge in surgical instrument according to various embodiments.

FIG. 24 is a flow diagram of a method of preventing reuse of a staple cartridge in surgical instrument that may be performed in conjunction with embodiments of the instrument 10 described above. At step 300, a first wireless signal is transmitted to the transponder 212, 264 and at step 305 a second wireless signal is received from the transponder 212, 264 such that one of a first electronic state and a second electronic state of the transponder 212, 264 may be determined based on the second wireless signal. In certain embodiments and as explained above, the wireless signals may be magnetic signals generated by inductive effects, although electric fields and electromagnetic fields may alternatively be employed. States of the transponder 212, 264 are indicative of states of the staple cartridge 38. In certain embodiments, for example, the first and second transponder states may indicate the unfired and fired states of the staple cartridge 38, respectively.

At step 310, if the first electronic state (indicative of an unfired staple cartridge state) is determined, the cutting instrument 34 may be enabled at step 315. After the instrument 10 is enabled, the operator may initiate a firing operation when ready.

At step 320, the transponder 212, 264 may be transitioned from the first electronic state to the second electronic state substantially simultaneously with an actuation of the cutting instrument 34. Accordingly, if an attempt is made to reuse the staple cartridge 38 at step 300, the second electronic state of the transponder 212, 264 (indicative of the fired staple cartridge state) may be determined at step 310 and a firing operation consequently prevented, as shown at step 325.

Above-described embodiments advantageously prevent operation of the instrument 10 when a spent staple cartridge 38 (or no staple cartridge 38) is present in the end effector 16, thus preventing cutting of tissue without simultaneous stapling. In addition to preventing operation of the instrument 10 under such circumstances, it may further be desirable to prevent operation of the instrument 10 after it has been used to perform a predetermined number of firing operations. Limiting the number of firing operations may be necessary, for example, so that use of the instrument 10 does not cause operational lifetimes of its various components (e.g., the cutting instrument 34, the battery 104, etc.) to be exceeded.

According to various embodiments, a limit on the number of firing operations may be implemented by the control unit 196 using, for example, a counter (not shown) contained within the processor 198. The counter may be incremented once for each firing operation indicated by one or more sensor inputs received by the control unit 196 (e.g., inputs received from the end-of-stroke and beginning-of-stroke sensors 156, 158 and the run-motor sensor 128). Subsequent to each firing operation, the processor 198 may compare the counter contents to a predetermined number. The predetermined number may be stored in the memory 200 of the processor 198 during instrument manufacture, for example, and represent the maximum number of firing operations performable by the instrument 10. The predetermined number may be determined based upon, among other things, operational lifetimes of the various instrument components and/or the expected requirements of a medical procedure for which the instrument 10 is to be used. When the counted number of firing operations is equal to the predetermined number, the control unit 196 may be configured to prevent additional firing operations by the instrument 10. In embodiments in which the control unit 196 directly or indirectly controls rotation of the motor 106 (e.g., via a PWM signal output in response to an input from the run-motor sensor 128), instruction code stored in the memory 200 may cause the processor 198 to prevent further output of power and/or control signals necessary for motor operation.

Figure 25:
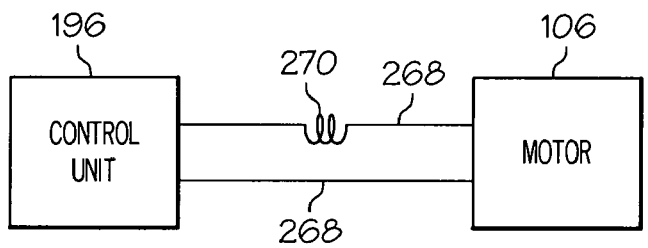
FIG. 25 is a block diagram of a circuit for preventing operation of the motor according to various embodiments.
Figure 26:
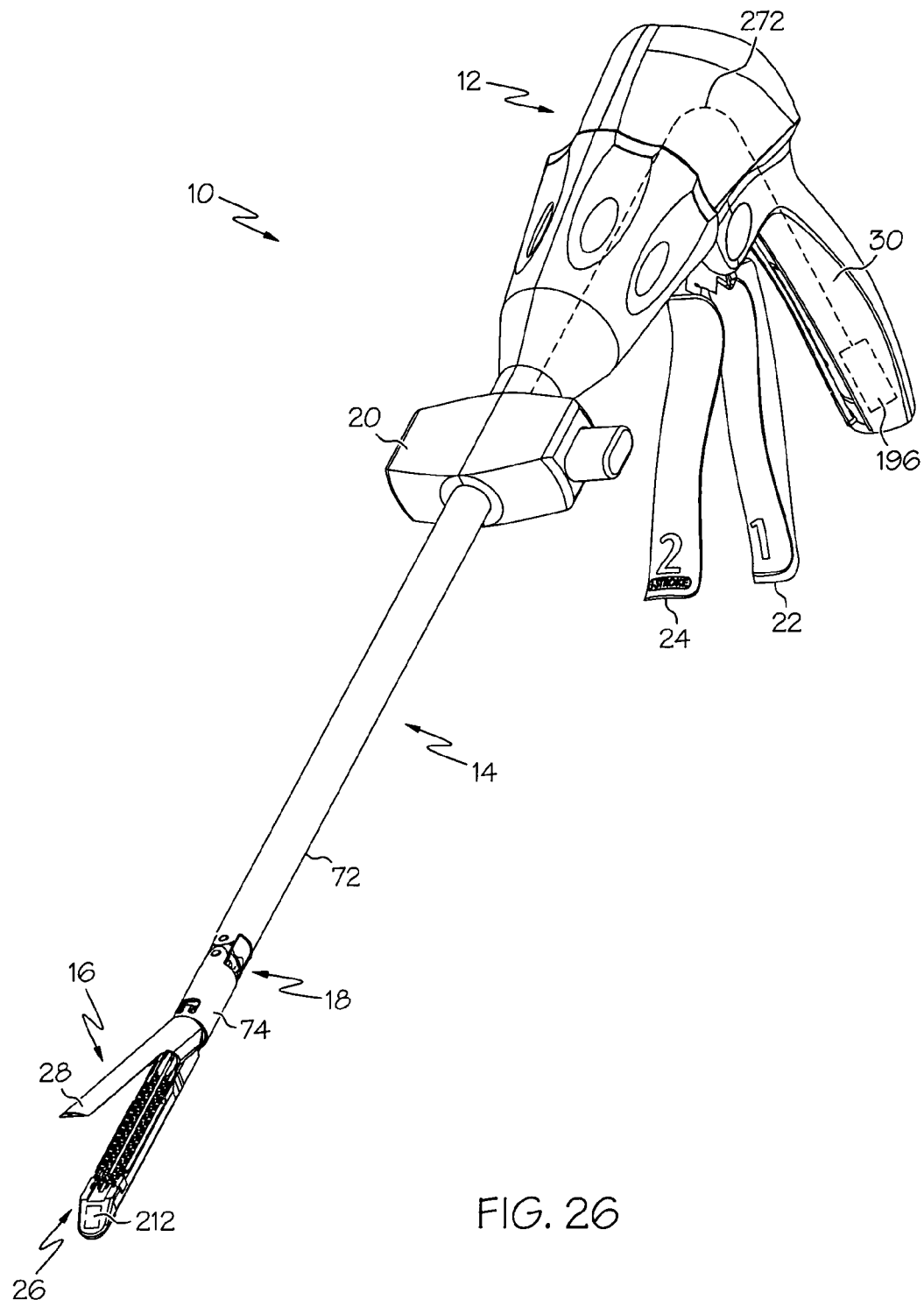

In other embodiments, the control unit 196 may prevent firing operations in excess of the predetermined number by disabling electronic components necessary for motor operation. For example, as shown in FIG. 25, the control unit 196 may be connected to the motor 106 via conductive leads 268, one of which includes an electronically-actuated fuse 270. Subsequent to the retraction of the cutting instrument 34 after the final firing operation (e.g., when the number of firing operations is equal to the predetermined number), the control unit 196 may cause increased current to be applied to the motor 106 such that the fuse 270 is opened (e.g., rendered non-conductive), thus preventing further motor operation. It will be appreciated that the placement of the fuse 270 is shown by way of example only, and that the fuse 270 may be connected in other ways to effect the same result. For example, the fuse 270 may be connected between the battery 104 and the electrical components of the instrument 10. In such embodiments, when the number of firing operations equals the predetermined number, the control unit 196 may short circuit the fuse 270 such that it is caused to open, thus removing power from the electrical components.

As an alternative to the fuse 270, it will be appreciated that a switch (e.g., a relay contact) controllable by a discrete output of the control unit 196 may be used instead. Additionally, it will be appreciated the control unit 196 may be configured to electronically disable one or more components necessary for motor operation (e.g., capacitors, transistors, etc.) other than a fuse by applying excessive voltages and/or currents thereto. Such components may be internal or external to the control unit 196.

Although above-described embodiments for limiting instrument use utilize a counter within the processor 198, it will be appreciated that other embodiments may utilize an electromechanical counter having a mechanical input suitably coupled to a component of the instrument 10 (e.g., the firing trigger 24) such that the counter is incremented once for each firing operation. The counter may include a set of electrical contacts that close (or open) when the counted number of firing operations exceeds a predetermined number stored within the counter. The contacts may serve as an input to the control unit 196, and the processor 198 may be programmed to enable or disable instrument operation based on the state of the contacts. Alternatively, the contacts may be connected to other components of the instrument (e.g., the battery 104 or the motor 106) such that power to the motor 106 is interrupted when the predetermined number of counts is exceeded.

In the embodiments described above, the battery 104 powers (at least partially) the firing operation of the instrument 10. As such, the instrument may be a so-called "power-assist" device. More details and additional embodiments of power-assist devices are described are described in pending U.S. patent application Ser. No. 11/343,573 referenced above, which is incorporated herein. It should be recognized, however, that the instrument 10 need not be a power-assist device and that this is merely an example of a type of device that may utilize aspects of the present invention. For example, the instrument 10 may include a user display (such as a LCD or LED display) that is powered by the battery 104 and controlled by the control unit 196. Data from the transponder 212, 264 in the end effector 16 may be displayed on such a display.

In another embodiment, the shaft 14 of the instrument 10, including for example, the proximate closure tube 72 and the distal closure tube 74, may collectively serve as part of an antenna for the control unit 196 by radiating signals to the transponder 212, 264 and receiving radiated signals from the transponder 212, 264. That way, signals to and from the transponder 212, 264 in the end effector 16 may be transmitted via the shaft 14 of the instrument 10.

The proximate closure tube 72 may be grounded at its proximate end by the exterior lower and upper side pieces 96, 98, which may be made of a nonelectrically conductive material, such as plastic. The drive shaft assembly components (including the main drive shaft 80 and secondary drive shaft 82) inside the proximate and distal closure tubes 72, 74 may also be made of a nonelectrically conductive material, such as plastic. Further, components of end effector 16 (such as the anvil 28 and the channel 26) may be electrically coupled to (or in direct or indirect electrical contact with) the distal closure tube 74 such that they may also serve as part of the antenna. Further, the transponder 212, 264 could be positioned such that it is electrically insulated from the components of the shaft 14 and end effector 16 serving as the antenna. For example, as discussed above, the transponder 212, 264 may be positioned in the staple cartridge 38, which may be made of a nonelectrically conductive material, such as plastic. Because the distal end of the shaft 14 (such as the distal end of the distal closure tube 74) and the portions of the end effector 16 serving as the antenna may be relatively close in distance to the transponder 212, 264, the power for the transmitted signals may be controlled such that interference with other systems in the use environment of the instrument 10 is reduced or minimized.

In such an embodiment, as shown in FIG. 22, the control unit 196 may be electrically coupled to the shaft 14 of the instrument 10, such as to the proximate closure tube 72, by a conductive link 272 (e.g., a wire). Portions of the outer shaft 14, such as the closure tubes 72, 74, may therefore act as part of an antenna for the control unit 196 by transmitting signals to the transponder 212, 264 and receiving signals transmitted by the transponder 212, 264. Signals received by the control unit 196 may be demodulated by the demodulator 204 and decoded by the decoder 206, as described above.

To transmit data signals to or from the transponder 212, 264 in the end effector 16, the link 272 may connect the control unit 196 to components of the shaft 14 of the instrument 10, such as the proximate closure tube 72, which may be electrically connected to the distal closure tube 74. The distal closure tube 74 is preferably electrically insulated from the transponder 212, 264, which may be positioned in the plastic staple cartridge 38. As mentioned before, components of the end effector 16, such as the channel 26 and the anvil 28, may be conductive and in electrical contact with the distal closure tube 74 such that they, too, may serve as part of the antenna.

With the shaft 14 acting as the antenna for the control unit 196, the control unit 196 can communicate with the transponder 212, 264 in the end effector 16 without a hardwired connection. In addition, because the distance between shaft 14 and the transponder 212, 264 is fixed and known, the power levels could be optimized to thereby minimize interference with other systems in the use environment of the instrument 10.

In another embodiment, the components of the shaft 14 and/or the end effector 16 may serve as an antenna for the transponder 212, 264. In such an embodiment, the transponder 212, 264 is electrically connected to the shaft 14 (such as to distal closure tube 74, which may be electrically connected to the proximate closure tube 72) and the control unit 196 is insulated from the shaft 14. For example, the transponder 212, 264 could be connected to a conductive component of the end effector 16 (such as the channel 26), which in turn may be connected to conductive components of the shaft (e.g., the closure tubes 72, 74). Alternatively, the end effector 16 may include a wire (not shown) that connects the transponder 212, 264 the distal closure tube 74.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example. The present invention also has application in conventional endoscopic and open surgical instrumentation as well as robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
    an end effector comprising a staple cartridge, the staple cartridge comprising a transponder; and
    a control unit disposed in a handle coupled to the end effector, the control unit comprising an inductive element to transmit and receive wireless signals, the control unit to:
        transmit a first wireless signal to the transponder and determine an electronic state of the transponder based on receipt or non-receipt of a second wireless signal from the transponder by the control unit in response to the transmission of the first wireless signal, wherein a first electronic state of the transponder corresponds to an unfired state of the staple cartridge, and wherein a second electronic state of the transponder corresponds to a fired state of the staple cartridge;
        enable actuation of a cutting instrument of the surgical instrument when the first electronic state is determined and prevent actuation of the cutting instrument when the second electronic state is determined; and
        transmit a third wireless signal to the transponder when the cutting instrument is actuated;
    wherein the transponder comprises at least one component electronically alterable by the transponder in response to receipt of the third wireless signal by the transponder to effect a transition of the transponder from the first electronic state to the second electronic state.

2. The surgical instrument of claim 1, wherein the end effector comprises:
    the cutting instrument;
    a longitudinally extending channel to removably seat the staple cartridge; and
    an anvil pivotally attached to the channel, wherein the object is positioned between the anvil and the channel;
    wherein when the cutting instrument is actuated a sled of the staple cartridge is engaged by the cutting instrument and driven longitudinally through the staple cartridge from an unfired position located at a proximal end of the staple cartridge to a fired position located at a distal end of the staple cartridge, the unfired position of the sled corresponding to the unfired state of the staple cartridge and the fired position of the sled corresponding to the fired state of the staple cartridge.

3. The surgical instrument of claim 1, wherein the at least one component is selected from the group consisting of: an electronically-actuated fuse, a thermally-actuated fuse, a capacitor, and a memory device.

4. The surgical instrument of claim 1, wherein the control unit is to determine the first electronic state or the second electronic state based on receipt of the second wireless signal by the control unit.

5. The surgical instrument of claim 1, wherein the control unit is to determine the first electronic state based on receipt of the second wireless signal by the control unit, and wherein the control unit is to determine the second electronic state based on nonreceipt of the second wireless signal by the control unit.

6. A staple cartridge for use in a surgical instrument, the staple cartridge comprising a transponder transitionable from a first electronic state to a second electronic state, wherein the first electronic state corresponds to an unfired state of the staple cartridge and wherein the second electronic state corresponds to a fired state of the staple cartridge, wherein the transponder is to indicate one of the electronic states based on a response or a nonresponse of the transponder to a first wireless signal transmitted by the surgical instrument.

7. The staple cartridge of claim 6, comprising a sled disposed within the staple cartridge to be engaged by a cutting instrument of the surgical instrument, wherein when engaged by the cutting instrument the sled is driven longitudinally through the staple cartridge from an unfired position located at a proximal end of the staple cartridge to a fired position located at a distal end of the staple cartridge, the unfired position of the sled corresponding to the unfired state of the staple cartridge and the fired position of the sled corresponding to the fired state of the staple cartridge.

8. The staple cartridge of claim 7, wherein the transponder comprises at least one component electronically alterable responsive to movement of the cutting instrument, the altered at least one component to effect a transition of the transponder from the first electronic state to the second electronic state.

9. The staple cartridge of claim 8, wherein the at least one component is selected from the group consisting of: a mechanically-actuated fuse and a switch.

10. The staple cartridge of claim 6, wherein the transponder is responsive to the first wireless signal transmitted by the surgical instrument to transmit a first wireless response signal when the transponder is in the first electronic state.

11. The staple cartridge of claim 10, wherein the transponder is responsive to the first wireless signal transmitted by the surgical instrument to transmit a second wireless response signal when the transponder is in the second electronic state.

12. The staple cartridge of claim 10, wherein the transponder is nonresponsive to the first wireless signal transmitted by the surgical instrument when the transponder is in the second electronic state.

13. The staple cartridge of claim 6, wherein the transponder comprises at least one component electronically alterable by the transponder responsive to a second wireless signal transmitted by the surgical instrument, the second wireless signal transmitted when the staple cartridge transitions from the unfired state to the fired state, the altered at least one component to effect a transition of the transponder from the first electronic state to the second electronic state.

14. The staple cartridge of claim 13, wherein the at least one component is selected from the group consisting of: an electronically-actuated fuse, a thermally-actuated fuse, a capacitor, and a memory device.

15. A surgical instrument, comprising:
    an end effector to receive a staple cartridge; and
    a control unit disposed in a handle coupled to the end effector, the control unit comprising an inductive element to transmit and receive wireless signals, the control unit to:
        transmit a first wireless signal to a transponder disposed within the staple cartridge and determine an electronic state of the transponder based on receipt or non-receipt of a second wireless signal from the transponder by the control unit in response to the transmission of the first wireless signal, wherein a first electronic state of the transponder corresponds to an unfired state of the staple cartridge, and wherein a second electronic state of the transponder corresponds to a fired state of the staple cartridge;
        enable actuation of a cutting instrument of the surgical instrument when the first electronic state is determined and prevent actuation of the cutting instrument when the second electronic state is determined; and
        transmit a third wireless signal to the transponder when the cutting instrument is actuated, the third wireless signal to effect a transition of the transponder from the first electronic state to the second electronic state.

16. The surgical instrument of claim 15, wherein the end effector comprises:
the cutting instrument;
a longitudinally extending channel to removably seat the staple cartridge; and
an anvil pivotally attached to the channel, wherein the object is positioned between the anvil and the channel;
wherein the cutting instrument engages a sled of the staple cartridge when actuated to drive the sled longitudinally through the staple cartridge from an unfired position located at a proximal end of the staple cartridge to a fired position located at a distal end of the staple cartridge, the unfired position of the sled corresponding to the unfired state of the staple cartridge and the fired position of the sled corresponding to the fired state of the staple cartridge.

17. A surgical instrument comprising:
an end effector comprising a staple cartridge, the staple cartridge comprising a transponder; and
a control unit disposed in a handle coupled to the end effector, the control unit comprising an inductive element to transmit and receive wireless signals, the control unit to:
transmit a first wireless signal to the transponder and determine an electronic state of the transponder-based on receipt or non-receipt of a second wireless signal from the transponder by the control unit in response to the transmission of the first wireless signal, wherein a first electronic state of the transponder corresponds to an unfired state of the staple cartridge, and wherein a second electronic state of the transponder corresponds to a fired state of the staple cartridge; and
enable actuation of a cutting instrument of the surgical instrument when the first electronic state is determined and prevent actuation of the cutting instrument when the second electronic state is determined;
wherein the transponder comprises at least one component electronically alterable by movement of the cutting instrument when actuated, the altered at least one component to effect a transition of the transponder from the first electronic state to the second electronic state.

18. A surgical instrument, comprising:
an end effector to receive a staple cartridge; and
a control unit disposed in a handle coupled to the end effector, the control unit comprising an inductive element to transmit and receive wireless signals, the control unit to:
transmit a first wireless signal to a transponder disposed within the staple cartridge and determine an electronic state of the transponder based on receipt or non-receipt of a second wireless signal from the transponder by the control unit in response to the transmission of the first wireless signal, wherein a first electronic state of the transponder corresponds to an unfired state of the staple cartridge, and wherein a second electronic state of the transponder corresponds to a fired state of the staple cartridge; and
enable actuation of a cutting instrument of the surgical instrument when the first electronic state is determined and prevent actuation of the cutting instrument when the second electronic state is determined;
wherein the cutting instrument, when actuated, electronically alters at least one component of the transponder to effect a transition of the transponder from the first electronic state to the second electronic state.

* * * * *